US009403854B2

(12) United States Patent
Grubbs et al.

(10) Patent No.: US 9,403,854 B2
(45) Date of Patent: Aug. 2, 2016

(54) CROSS-METATHESIS REACTION OF FUNCTIONALIZED AND SUBSTITUTED OLEFINS USING GROUP 8 TRANSITION METAL CARBENE COMPLEXES AS METATHESIS CATALYSTS

(71) Applicant: CALIFORNIA INSTITUTE OF TECHNOLOGY, Pasadena, CA (US)

(72) Inventors: Robert H. Grubbs, South Pasadena, CA (US); Arnab K. Chatterjee, Pasadena, CA (US); Tae-Lim Choi, Pasadena, CA (US); Steven D. Goldberg, Pasadena, CA (US); Jennifer A. Love, Pasadena, CA (US); John P. Morgan, Pasadena, CA (US); Daniel P. Sanders, Pasadena, CA (US); Matthias Scholl, Cambridge, MA (US); F. Dean Toste, Pasadena, CA (US); Tina M. Trnka, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/055,442

(22) Filed: Oct. 16, 2013

(65) Prior Publication Data
US 2014/0288319 A1 Sep. 25, 2014

Related U.S. Application Data

(63) Continuation of application No. 10/114,418, filed on Apr. 1, 2002, now abandoned.

(60) Provisional application No. 60/280,590, filed on Mar. 30, 2001, provisional application No. 60/280,462, filed on Mar. 30, 2001, provisional application No. 60/284,213, filed on Apr. 16, 2001, provisional application No. 60/285,597, filed on Apr. 20, 2001, provisional application No. 60/340,588, filed on Dec. 14, 2001.

(51) Int. Cl.
| C07D 233/02 | (2006.01) |
| C07D 233/12 | (2006.01) |
| C07F 9/40 | (2006.01) |
| C07C 6/04 | (2006.01) |
| C07C 17/275 | (2006.01) |
| C07C 29/40 | (2006.01) |
| C07C 45/69 | (2006.01) |
| C07C 67/293 | (2006.01) |
| C07C 67/343 | (2006.01) |
| C07C 67/475 | (2006.01) |
| C07C 319/20 | (2006.01) |
| C07D 263/14 | (2006.01) |
| C07D 317/12 | (2006.01) |
| C07D 317/20 | (2006.01) |
| C07D 317/24 | (2006.01) |
| C07F 7/18 | (2006.01) |
| C07F 15/00 | (2006.01) |

(Continued)

(52) U.S. Cl.
CPC ... *C07F 9/40* (2013.01); *C07C 6/04* (2013.01); *C07C 17/275* (2013.01); *C07C 29/40* (2013.01); *C07C 29/46* (2013.01); *C07C 41/14* (2013.01); *C07C 45/69* (2013.01); *C07C 67/293* (2013.01); *C07C 67/297* (2013.01); *C07C 67/343* (2013.01); *C07C 67/475* (2013.01); *C07C 201/12* (2013.01); *C07C 319/20* (2013.01); *C07D 263/14* (2013.01); *C07D 317/12* (2013.01); *C07D 317/20* (2013.01); *C07D 317/24* (2013.01); *C07F 7/1892* (2013.01); *C07F 9/4015* (2013.01); *C07F 15/0046* (2013.01); *C07C 2101/14* (2013.01); *C07C 2101/16* (2013.01); *C07C 2103/74* (2013.01); *C07C 2531/22* (2013.01)

(58) Field of Classification Search
CPC ............................. C07D 233/02; C07D 233/12
See application file for complete search history.

(56) References Cited

U.S. PATENT DOCUMENTS

| 5,342,909 A | 8/1994 | Grubbs et al. |
| 5,750,815 A | 5/1998 | Grubbs et al. |

(Continued)

FOREIGN PATENT DOCUMENTS

| WO | WO 96/20796 | 7/1996 |
| WO | WO 99/51344 A1 | 10/1999 |

(Continued)

OTHER PUBLICATIONS

Chatterjee, 2001, Synlett, p. 1034-1037.*
Connon, 2003, Angew. Chem. Int. Ed., vol. 42, p. 1900-1923.*
Sing et al., "Effect of indole ethyl isothiocyanates on proliferation, apoptosis, and MAPK signaling in neuroblastoma cell lines," *Bioorganic & Medicinal Chemistry Letters* 17:5846-5852 (2007).

(Continued)

*Primary Examiner* — Michael Barker
*Assistant Examiner* — Karen Cheng
(74) *Attorney, Agent, or Firm* — J.A. Lindeman & Co., PLLC

(57) ABSTRACT

The invention pertains to the use of Group 8 transition metal carbene complexes as catalysts for olefin cross-metathesis reactions. In particular, ruthenium and osmium alkylidene complexes substituted with an N-heterocyclic carbene ligand are used to catalyze cross-metathesis reactions to provide a variety of substituted and functionalized olefins, including phosphonate-substituted olefins, directly halogenated olefins, 1,1,2-trisubstituted olefins, and quaternary allylic olefins. The invention further provides a method for creating functional diversity using the aforementioned complexes to catalyze cross-metathesis reactions of a first olefinic reactant, which may or may not be substituted with a functional group, with each of a plurality of different olefinic reactants, which may or may not be substituted with functional groups, to give a plurality of structurally distinct olefinic products. The methodology of the invention is also useful in facilitating the stereoselective synthesis of 1,2-disubstituted olefins in the cis configuration.

8 Claims, No Drawings

(51) Int. Cl.
*C07C 201/12* (2006.01)
*C07C 29/46* (2006.01)
*C07C 41/14* (2006.01)
*C07C 67/297* (2006.01)

(56) References Cited

U.S. PATENT DOCUMENTS

| | | | |
|---|---|---|---|
| 5,831,108 | A | 11/1998 | Grubbs et al. |
| 5,969,170 | A | 10/1999 | Grubbs et al. |
| 6,080,826 | A | 6/2000 | Grubbs et al. |
| 6,111,121 | A | 8/2000 | Grubbs et al. |
| 6,211,391 | B1 | 4/2001 | Grubbs et al. |
| 6,215,019 | B1 | 4/2001 | Pederson et al. |
| 6,306,988 | B1 | 10/2001 | Grubbs et al. |
| 2001/0039360 | A1 | 11/2001 | Grubbs et al. |
| 2002/0013473 | A1 | 1/2002 | Grubbs et al. |

FOREIGN PATENT DOCUMENTS

| | | |
|---|---|---|
| WO | WO 00/71554 A2 | 11/2000 |
| WO | WO 01/36368 A2 | 5/2001 |
| WO | WO 02/00590 A1 | 1/2002 |
| WO | WO 02/094748 A1 | 11/2002 |

OTHER PUBLICATIONS

Chatterjee et al., "Synthesis of Trisubstituted Alkenes via Olefin Cross-Metathesis," *Organic Letters* 1(11):1751-1753 (1999).
Blackwell et al., "New Approaches to Olefin Cross-Metathesis," *J. Am. Chem. Soc.* 122(1):58-71 (2000).
Chatterjee et al., "Synthesis of Functionalized Olefins by Cross and Ring-Closing Metatheses," *J. Am. Chem. Soc.* 122(15):3783-3784 (2000).
Choi et al., "Olefin Metathesis Involving Ruthenium Enoic Carbene Complexes," *J. Am. Chem. Soc.* 123(42):10417-10418 (2001).
Goldberg et al., "A One-Pot Cross-Metathesis/Allylboration Reaction: A Three-Component Coupling for the Synthesis of Functionalized Homoallylic Alcohols," Angew. Chem. Int. Ed. 41(5):807-810 (2002).
Lee et al., "A Strategy for Macrocyclic Ring Closure and Functionalization Aimed Toward Split-Pool Syntheses," *J. Am. Chem. Soc.* 121(45):10648-10649 (1999).
Toste et al., "Functional Group Diversity by Ruthenium-Catalyzed Olefin Cross-Metathesis," *Pure Appl. Chem.* 74(1):7-10 (2002).
Trnka et al., "The Development of $L_2X_2Ru=CHR$ Olefin Metathesis Catalysts: An Organometallic Success Story," *Accounts of Chemical Research* 34(1):18-29 (2001).
Wilhelm et al., "Reactivity of $Ru(H)(H_2)Cl(PCy_3)_2$ with Propargyl and Vinyl Chlorides: New Methodology to Give Metathesis-Active Ruthenium Carbenes," *Organometallics* 16(18):3867-3869 (1997).

* cited by examiner

CROSS-METATHESIS REACTION OF FUNCTIONALIZED AND SUBSTITUTED OLEFINS USING GROUP 8 TRANSITION METAL CARBENE COMPLEXES AS METATHESIS CATALYSTS

CROSS-REFERENCE TO RELATED APPLICATIONS

This application is a Continuation of application Ser. No. 10/114,418 filed Apr. 1, 2002, which claims priority under 35 U.S.C. §119(e)(1) to the following provisional U.S. patent applications: Ser. No. 60/280,590, filed Mar. 30, 2001; Ser. No. 60/280,462, filed Mar. 30, 2001; Ser. No. 60/284,213, filed Apr. 16, 2001; Ser. No. 60/285,597, filed Apr. 20, 2001; and Ser. No. 60/340,588, filed Dec. 14, 2001. The disclosures of the aforementioned applications are incorporated by reference in their entireties.

ACKNOWLEDGEMENT OF GOVERNMENT SUPPORT

This invention was made with government support under Grant No. GM031332 awarded by the National Institutes of Health and Grant No. 9809856 awarded by the National Science Foundation. The government has certain rights in the invention.

TECHNICAL FIELD

This invention relates generally to a method for carrying out an olefin metathesis reaction using a Group 8 transition metal complex as a catalyst, and more particularly relates to a method for carrying out cross-metathesis reactions using the aforementioned catalyst wherein at least one of the olefinic reactants is a functionalized olefin, a geminal disubstituted olefin, a trisubstituted olefin, and/or a quaternary allylic olefin. Methods are also provided for the catalysis of stereoselective olefin metathesis reactions, and for the creation of chemical diversity by carrying out a plurality of olefin metathesis reactions using a single olefinic substrate and different metathesis partners, to generate a plurality of structurally distinct products.

BACKGROUND OF THE INVENTION

To the synthetic organic or polymer chemist, simple methods for forming carbon-carbon bonds are extremely important and valuable tools. One method of C—C bond formation that has proved particularly useful is transition-metal catalyzed olefin metathesis. "Olefin metathesis," as is understood in the art, refers to the metal-catalyzed redistribution of carbon-carbon bonds. See Trnka and Grubbs (2001) *Acc. Chem. Res.* 34:18-29. Over two decades of intensive research effort has culminated in the discovery of well-defined ruthenium and osmium carbenes that are highly active olefin metathesis catalysts and stable in the presence of a variety of functional groups.

These ruthenium and osmium carbene complexes have been described in U.S. Pat. Nos. 5,312,940, 5,342,909, 5,831,108, 5,969,170, 6,111,121, and 6,211,391 to Grubbs et al., assigned to the California Institute of Technology. The ruthenium and osmium carbene complexes disclosed in these patents all possess metal centers that are formally in the +2 oxidation state, have an electron count of 16, and are pentacoordinated. These catalysts are of the general formula (I)

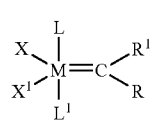

where M is a Group 8 transition metal such as ruthenium or osmium, X and X' are anionic ligands, L and L' are neutral electron donors, and R and R' are specific substituents, e.g., one may be H and the other may be a substituted or unsubstituted hydrocarbyl group such as phenyl or $C=C(CH_3)_2$. Such complexes have been disclosed as useful in catalyzing a variety of olefin metathesis reactions, including ring opening metathesis polymerization ("ROMP"), ring closing metathesis ("RCM"), acyclic diene metathesis polymerization ("ADMET"), ring-opening metathesis ("ROM"), and cross-metathesis ("CM" or "XMET") reactions.

For the most part, such metathesis catalysts have been prepared with phosphine ligands, e.g., triphenylphosphine or dimethylphenylphospine, exemplified by the well-defined, metathesis-active ruthenium alkylidene complexes (II) and (III)

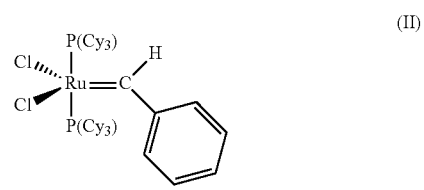

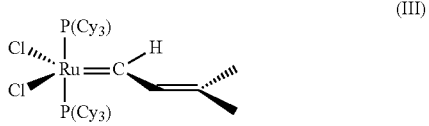

wherein "Cy" is a cycloalkyl group such as cyclohexyl or cyclopentyl. See U.S. Pat. No. 5,917,071 to Grubbs et al. and Trnka and Grubbs, cited supra. These compounds are highly reactive catalysts useful for catalyzing a variety of olefin metathesis reactions, and are tolerant of many different functional groups. However, as has been recognized by those in the field, the compounds display low thermal stability, decomposing at relatively low temperatures. Jafarpour and Nolan (2000) *Organometallics* 19(11):2055-2057.

Recently, however, significant interest has focused on the use of N-heterocyclic carbene ligands as superior alternatives to phosphines. See, e.g., Trnka and Grubbs, supra; Bourissou et al. (2000) *Chem. Rev.* 100:39-91; Scholl et al. (1999) *Tetrahedron Lett.* 40:2247-2250; Scholl et al. (1999) *Organic Lett.* 1(6):953-956; and Huang et al. (1999) *J. Am. Chem. Soc.* 121:2674-2678. N-heterocyclic carbene ligands offer many advantages, including readily tunable steric bulk, vastly increased electron donor character, and compatibility with a variety of metal species. In addition, replacement of one of the phosphine ligands in these complexes significantly improves thermal stability. The vast majority of research on these carbene ligands has focused on their generation and isolation, a feat finally accomplished by Arduengo and coworkers within the last ten years (see, e.g., Arduengo et al. (1999) *Acc. Chem. Res.* 32:913-921). Representative of these second generation catalysts are the four ruthenium complexes (IVA), (IVB), (VA) and (VB):

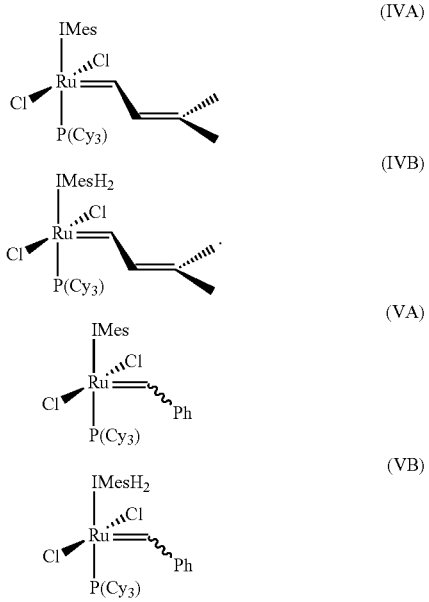

In the above structures, Cy is as defined previously, "IMes" represents 1,3-dimesityl-imidazol-2-ylidene

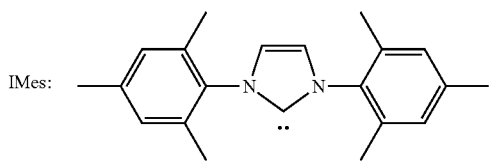

and "IMesH₂" represents 1,3-dimesityl-4,5-dihydroimidazol-2-ylidene

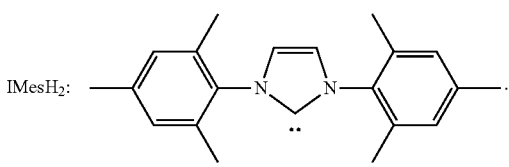

Other complexes formed from N-heterocyclic carbene ligands are also known.

These transition metal carbene complexes, particularly those containing a ligand having the 4,5-dihydroimidazol-2-ylidene structure, such as in IMesH₂, have been found to address a number of previously unsolved problems in olefin metathesis reactions, particularly cross-metathesis reactions. These problems span a variety of reactions and starting materials. The following discussion focuses on representative problems in the art that have now been addressed by way of the present invention.

Use of Olefinic Phosphonates and Other Functionalized Olefins as Cross-Metathesis Reactants: Olefins that contain phosphonate functionality are used extensively in synthetic organic chemistry. For example, allylic phosphonates are employed in the preparation of dienes and polyenes by Horner-Emmons olefination, providing products with improved stereoselectivity as compared to the corresponding phosphonium salts; see Crombie et al. (1969) *J. Chem. Soc., Chem. Commun.* at 1024; and Whang et al. (1992) *J. Org. Chem.* 56:7177. The reaction of organic halides with trialkyl phosphites (Michaelis-Arbuzov reaction) is used primarily for the synthesis of allylphosphonates; see Bhattacharya et al. (1981) *Chem. Rev.* 81:415. However, elimination and/or loss of olefin stereochemical integrity are often competitive with product formation. Palladium catalyzed cross-coupling of hydrogen phosphonates to conjugated dienes and allenes has also been developed, but requires high reaction temperatures and provide low regioselectivity in highly substituted phosphonates products. See Hirao et al. (1980) *Tetrahedron Lett.* 21:3595; Hirao et al. (1982) *Bull. Chem. Soc. Jpn.* 55: 909; Imamoto et al. (1990) *J. Am. Chem. Soc.* 112:5244; Zhao et al. (2000) *Organometallics* 19:4196.

Vinylphosphonates are important synthetic intermediates and have been investigated as biologically active compounds. Vinylphosphonates have been used as intermediates in stereoselective synthesis of trisubstituted olefins and in heterocycle synthesis; see Shen et al. (2000) *Synthesis*, p. 99; Tago et al. (2000) *Org. Lett.* 2:1975; Kouno et al. (1998) *J. Org. Chem.* 63:6239; and Kouno et al. (2000) *J. Org. Chem.* 65:4326. The synthesis of vinylphosphonates has also been widely examined and a variety of non-catalytic approaches have been described in the literature. Recent metal-catalyzed methods include palladium catalyzed cross-coupling (see, e.g., Holt et al. (1989), *Tetrahedron Lett.* 30:5393; Han et al. (1996), *J. Am. Chem. Soc.* 118:1571; Kazankova et al. (1999), *Tetrahedron Lett.* 40:569; Okauchi et al. (1999), *Tetrahedron Lett.* 40:5337; Zhong et al. (2000), *Synth. Commun.* 30:273; and Han et al. (2000), *J. Am. Chem. Soc.* 122:5407) and Heck coupling of aryldiazonium salts with vinyl phosphonates (Brunner et al. (2000) *Synlett*. at p. 201), but are limited by the requirement of highly reactive functional groups in the substrates. Therefore, a more mild, general and stereoselective method for the synthesis of vinyl and allylphosphonates using commercially available starting materials would be quite valuable, and would provide an additional degree of orthogonality to the previously reported syntheses. An ideal such method would also be applicable in other contexts as well, for example in the synthesis of olefins substituted with functional groups other than phosphonates. The invention, in one embodiment, is directed to this pressing need in the art, and provides a method that not only accomplishes the aforementioned goals, but is also useful in a more generalized process for creating functional group diversity in a population of olefinic products prepared using cross-metathesis.

Cross-Metathesis of α-Halogenated Olefins and Synthesis of Directly Halogenated Olefins: Since the discovery of the olefin metathesis reaction in the 1950s, the metathesis of halogen-containing olefins has received very little attention. The metathesis of allyl bromide, allyl chloride, and related substrates with the heterogeneous Re₂O₇/Al₂O₃/Me₄Sn catalyst system are among the few examples. Kawai et al. (1998) *J. Mol. Catal. A* 133:51; Bogolepova et al. (1992) *Petrol. Chem.* 32:461; Mol et al. (1979) *J. Chem. Soc. Chem. Commun.*, at pp. 330-331 Nakamura et al. (1977) *Chem. Lett.*, at p. 1127; Fridman et al. (1997) *Doklady Akad. Nauk S.S.S.R.* 234:1354. Most recently, the cross-metathesis of 3,3,4,4,5,5,6,6,6-nonafluoro-1-hexene with terminal olefin and the dimerization of vinyl gem-difluorocyclopropane derivatives have been achieved using catalyst (VB). Chatterjee et al. (2000) *J. Am. Chem. Soc.* 122:3783; International Patent Publication No. WO 02/00590 to Grubbs et al.; Itoh et al. (2000) *Org. Lett.* 2:1431. In these cases, the substrates are challenging because of the electron-withdrawing nature of the pendent halogens. A particularly challenging situation arises when the olefin is directly halogenated, because the metathesis reaction will then involve a monohalo [M]=CXR or dihalo [M]=CX$_2$ carbene complex as the propagating species (where X=halide), rather than the more usual alkylidene [M]=CR$_2$ (where R=H, alkyl, aryl). To the best of applicants' knowledge, there has been only one report of metathesis involving directly halogenated olefins, namely the cross-metathesis of 1-chloro- and 1-bromoethylene with propylene using Re$_2$O$_7$/Al$_2$O$_3$/Me$_4$Sn (Fridman et al. (1977) *Doklady Akad. Nauk S.S.S.R.* 234:1354).

Accordingly, there are very few methods available for the mild and selective synthesis of directly halogenated olefins, and in particular, directly fluorinated olefins. The present invention now provides a straightforward method for carrying out an olefin metathesis reaction using an α-halogenated olefin, which may be an α-fluorinated olefin, in order to provide a directly halogenated (e.g., fluorinated) olefinic product.

Catalyzed Cross-Metathesis of Highly Substituted Olefins, Including Geminal Disubstituted Olefins and Quaternary Allylic Olefins: In prior applications of olefin metathesis, particularly olefin cross-metathesis, there has been no method available for generation of highly substituted olefins, such as trisubstituted olefins (wherein the substituents may be the same or different) and olefins that contain quaternary carbons at the allylic position. Trisubstituted and quaternary allylic olefinic substituents are, of course, present in a diverse array of organic molecules, including pharmaceuticals, natural products, and functionalized polymers, and the difficulty in generating such compounds has been a substantial limitation. The methodology of the present invention overcomes this limitation and now provides an efficient and versatile way to synthesize 1,1,2-trisubstituted olefins as well as 1,2-disubstituted olefins containing one quaternary allylic carbon atom.

Stereoselective Synthesis of 1,2-Disubstituted Olefins Via Cross-Metathesis: Another limitation in known olefin metathesis reactions is that there is no general method for controlling the stereoselectivity of the newly formed olefins. In many cases, the more thermodynamically stable trans olefin geometry was selectively formed, with minimal, if any, of the cis olefin produced. See Blackwell et al. (2000), "New approaches to olefin cross-metathesis," *J. Am. Chem. Soc.* 122(1):58-71; and Chatterjee et al. (2000), "Synthesis of functionalized olefins by cross and ring-closing metathesis," *J. Am. Chem. Soc.* 122(15):3783-3784. The present invention also addresses this need in the art by providing a stereoselective method for synthesizing a 1,2-disubstituted olefin in primarily the cis configuration.

SUMMARY OF THE INVENTION

The present invention is addressed to the aforementioned needs in the art, and provides a novel process for using certain Group 8 transition metal complexes to catalyze a variety of olefin metathesis reactions, primarily cross-metathesis reactions. The complexes used are metal carbenes comprised of a Group 8 transition metal, particularly ruthenium or osmium, which preferably, although not necessarily, contain an N-heterocyclic carbene ligand. Such complexes are highly active catalysts of olefin metathesis reactions, including the cross-metathesis reactions described in detail herein. In contrast to previous catalysts used in olefin cross-metathesis, the present complexes allow an olefinic reactant to be substituted with a functional group without compromising the efficiency or selectivity of a metathesis reaction involving that olefin. The present invention also allows the second reactant, i.e., the olefin metathesis partner, to be substituted with a functional group. The functional group may or may not be a ligand for the metal complex; the present method is not limited in this regard. The olefinic reactant may also be di-substituted at one of the olefinic carbon atoms, as is the case with 2-methyl-2-butene, for example, or may be a quaternary allylic olefin, i.e., an olefin directly substituted at one or both of the olefinic carbon atoms with the moiety —CH$_2$—CR$_3$ where R is other than hydrogen.

These cross-metathesis reactions are carried out with a catalyst having the structure of formula (VI)

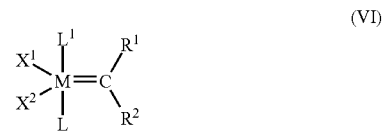

(VI)

in which:

M is a Group 8 transition metal, particularly Ru or Os;

X$^1$ and X$^2$ may be the same or different, and are anionic ligands or polymers;

R$^1$ is selected from the group consisting of hydrogen, hydrocarbyl, substituted hydrocarbyl, heteroatom-containing hydrocarbyl, substituted heteroatom-containing hydrocarbyl, and carboxyl;

R$^2$ is selected from the group consisting of hydrogen, hydrocarbyl, substituted hydrocarbyl, heteroatom-containing hydrocarbyl, and substituted heteroatom-containing hydrocarbyl;

L is a neutral electron donor ligand; and

L$^1$ is a neutral electron donor ligand having the structure of formula (VII)

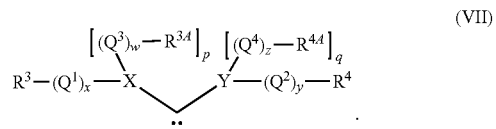

(VII)

In structure (VII):

X and Y are heteroatoms selected from N, O, S, and P;

p is zero when X is O or S, and is 1 when X is N or P;

q is zero when Y is O or S, and is 1 when Y is N or P;

Q$^1$, Q$^2$, Q$^3$, and Q$^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—;

w, x, y and z are independently zero or 1; and

R$^3$, R$^{3A}$, R$^4$, and R$^{4A}$ are independently selected from the group consisting of hydrogen, hydrocarbyl, substituted hydrocarbyl, heteroatom-containing hydrocarbyl, and substituted heteroatom-containing hydrocarbyl, wherein any two or more of X$^1$, X$^2$, L, R$^1$, R$^2$, R$^3$, R$^{3A}$, R$^4$, and R$^{4A}$ can be taken together to form a chelating multidentate ligand.

Accordingly, the complex of formula (V) may also be represented as (VIA)

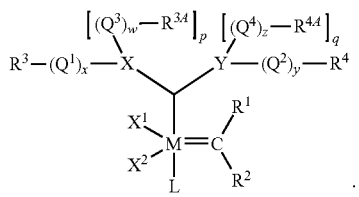

In a preferred embodiment, L is an N-heterocyclic carbene having the structure of formula (VIIA)

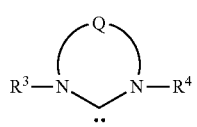

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage. Accordingly, the metal carbene complex of formula (VIA) may also be represented as follows:

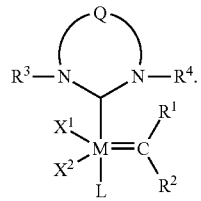

In one embodiment, then, a method is provided for synthesizing olefins substituted with a functional group by cross-metathesis using a Group 8 transition metal catalyst having the structure of formula (VI). At least one of the two olefinic reactants is substituted with one or more functional groups, which may or may not be in protected form (e.g., a hydroxyl group may be protected as an acyloxy or benzyloxy group). More specifically, at least one of the two olefinic reactants has the structure of formula (VIII)

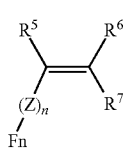

wherein:

Fn is a functional group such as phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, carbamoyl, epoxy, styrenyl, silyl, silyloxy, silanyl, siloxazanyl, boronato, or boryl, or a metal-containing or metalloid-containing group (wherein the metal may be, for example, Sn or Ge);

n is zero or 1;

Z is a hydrocarbylene or a substituted and/or heteroatom-containing hydrocarbylene linking group such as an alkylene, substituted alkylene, heteroalkylene, substituted heteroalkene, arylene, substituted arylene, heteroarylene, or substituted heteroarylene linkage; and $R^5$, $R^6$, and $R^7$ are independently selected from the group consisting of hydrogen, —(Z)$_n$-Fn, hydrocarbyl, substituted hydrocarbyl, heteroatom-containing hydrocarbyl, and substituted heteroatom-containing hydrocarbyl, and, if substituted hydrocarbyl or substituted heteroatom-containing hydrocarbyl, wherein one or more of the substituents may be —(Z)$_n$-Fn.

In one preferred embodiment, Fn is a phosphonate and Z is $CH_2$, such that the reactant is an allylphosphonate (when n is 1) and a vinylphosphonate (when n is zero). The product of the cross-metathesis reaction is also an olefin substituted with a —(Z)$_n$-Fn group.

In another embodiment, a method is provided for synthesizing directly halogenated olefins by cross-metathesis using a catalyst having the structure of formula (VI). In this embodiment, at least one of the olefinic reactants has the structure of formula (IX)

wherein $X^3$ is halo, and $R^8$, $R^9$, and $R^{10}$ are independently selected from the group consisting of hydrogen, halo, hydrocarbyl, substituted hydrocarbyl, heteroatom-containing hydrocarbyl, substituted heteroatom-containing hydrocarbyl, and —(Z)$_n$-Fn where n, Z and Fn are as defined above.

In a further embodiment, a method is provided for synthesizing substituted olefins, particularly trisubstituted and quaternary allylic olefins, wherein the method comprises using the complex of formula (VI) to catalyze a cross-metathesis reaction between a geminal disubstituted olefin or a quaternary allylic olefin, and a second olefin. If it is a geminal disubstituted olefin, the first olefin has the structure (X)

wherein $R^{11}$, $R^{12}$, $R^{13}$, and $R^{14}$ are selected from the group consisting of hydrogen, hydrocarbyl, substituted hydrocarbyl, heteroatom-containing hydrocarbyl, substituted heteroatom-containing hydrocarbyl, and —(Z)$_n$-Fn where n, Z and Fn are as defined above, with the proviso that $R^{11}$ and $R^{12}$, or $R^{13}$ and $R^{14}$, are other than hydrogen. If it is a quaternary allylic olefin, the first olefin has the structure (XI)

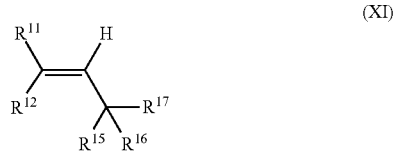

(XI)

wherein $R^{11}$ and $R^{12}$ are as defined previously, and $R^{15}$, $R^{16}$, and $R^{17}$ are any nonhydrogen substituents, e.g., alkyl, aryl, heteroalkyl, heteroaryl, —$(Z)_n$-Fn (where n, Z, and Fn are as defined above with respect to formula (VIII)), or the like.

In the above-described embodiments, the second olefin has a molecular structure given by $R^{18}R^{19}C=CR^{20}R^{21}$ wherein $R^{18}$, $R^{19}$, $R^{20}$, and $R^{21}$ may be hydrogen, hydrocarbyl, substituted hydrocarbyl, heteroatom-containing hydrocarbyl, substituted heteroatom-containing hydrocarbyl, —$(Z)_n$-Fn, etc. As such, it will be appreciated that the second olefin may have a molecular structure encompassed by any one of the above generic formulae (VIII), (IX), (X), and (XI), or may be a simple structure such as ethylene per se.

The invention is additionally useful in providing a method for controlling the stereoselectivity of an olefin cross-metathesis reaction, and in providing a cross-metathesis product in which the thermodynamically less favored cis configuration predominates. The reaction is carried out using selected olefinic reactants, with one olefinic reactant substituted in a 1,2-cis configuration. The catalyst used has the structure of formula (VI), with $R^3$ and $R^4$ representing bulky ligands, e.g., bicyclic or polycyclic ligands that may or may not be aromatic.

In a still further embodiment of the invention, complexes of formula (VI) are used to catalyze a plurality of cross-metathesis reactions from a common olefinic reactant to generate chemical diversity, i.e., to provide a plurality of products having related structures but retaining a distinguishing feature, such that each synthesized compound is different from each other synthesized compound. Each olefinic reactant can be substituted with functional groups, yielding cross-metathesis products containing those groups, and thus providing the option of further derivatization. While prior olefin cross-metathesis reactions have been used to synthesize alkenes bearing a range of functional groups, these prior reactions have been limited to olefins that do not contain any functional groups that could behave as ligands for the catalyst employed. By contrast, the present method can be used with olefinic starting materials in which functional groups are present that could act as ligands for the metal complex selected as a metathesis catalyst.

DETAILED DESCRIPTION OF THE INVENTION

I. Definitions and Nomenclature:

It is to be understood that unless otherwise indicated this invention is not limited to specific reactants, reaction conditions, ligands, metal complexes, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a compound" encompasses a combination or mixture of different compounds as well as a single compound, reference to "a functional group" includes a single functional group as well as two or more functional groups that may or may not be the same, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched or cyclic saturated hydrocarbon group typically although not necessarily containing 1 to about 20 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched or cyclic alkyl group, where "alkyl" is as defined above.

The term "alkenyl" as used herein refers to a linear, branched or cyclic hydrocarbon group of 2 to 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched or cyclic alkenyl group, where "alkenyl" is as defined above.

The term "alkynyl" as used herein refers to a linear or branched hydrocarbon group of 2 to 20 carbon atoms containing at least one triple bond, such as ethynyl, n-propynyl, and the like. Preferred alkynyl groups herein contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain one aromatic ring or 2 to 4 fused or linked aromatic rings, e.g., phenyl, naphthyl, biphenyl, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom. Unless otherwise indicated, the terms "aromatic," "aryl," and "arylene" include heteroaromatic, substituted aromatic, and substituted heteroaromatic species.

The term "aryloxy" as used herein refers to an aryl group bound through a single, terminal ether linkage. An "aryloxy" group may be represented as —O-aryl where aryl is as defined above.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The term "alicyclic" refers to an aliphatic cyclic moiety, which may or may not be bicyclic or polycyclic.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

"Hydrocarbyl" refers to univalent hydrocarbyl radicals containing 1 to about 30 carbon atoms, preferably 1 to about 20 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, and the term "hydrocarbylene" intends a divalent hydrocarbyl moiety containing 1 to about 30 carbon atoms, preferably 1 to about 20 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety at least one hydrogen atom bound to a carbon (or other) atom is replaced with one or more non-hydrogen substituents. Examples of such substituents include, without limitation: functional groups such as halogen, phosphonato, phosphoryl, phosphanyl, phosphino, sulfonato, $C_1$-$C_{20}$ alkylsulfanyl, $C_5$-$C_{20}$ arylsulfanyl $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, carbamoyl, epoxy, styrenyl, silyl, silyloxy, silanyl, siloxazanyl, boronato, or boryl, or a metal-containing or metalloid-containing group (wherein the metal may be, for example, Sn or Ge); and the hydrocarbyl moieties $C_1$-$C_{20}$ alkyl, $C_2$-$C_{20}$ alkenyl, $C_2$-$C_{20}$ alkynyl, $C_5$-$C_{20}$ aryl, $C_5$-$C_{30}$ aralkyl, and $C_5$-$C_{30}$ alkaryl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "amino" is used herein to refer to the group —$NZ^1Z^2$, where each of $Z^1$ and $Z^2$ is independently selected from the group consisting of hydrogen and optionally substituted alkyl, alkenyl, alkynyl, aryl, aralkyl, alkaryl and heterocyclic.

The term "stereoselective" refers to a chemical reaction that preferentially results in one stereoisomer relative to a second stereoisomer, i.e., gives rise to a product of which the ratio of a desired stereoisomer to a less desired stereoisomer is greater than 1:1.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

II. The Catalyst:

The cross-metathesis reactions of the invention are carried out catalytically, using a Group 8 transition metal complex that preferably contains two different ligands. These transition metal carbene complexes include a metal center in a +2 oxidation state, have an electron count of 16, and are pentacoordinated. More specifically, the preferred catalysts herein have the structure of formula (VIA)

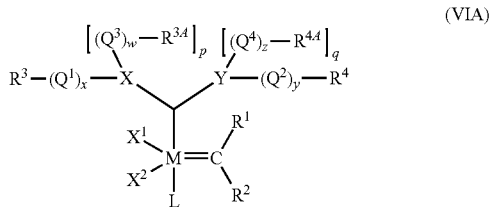

wherein the various substituents are as follows:

M, which serves as the transition metal center in the +2 oxidation state, is a Group 8 transition metal, particularly ruthenium or osmium. In a preferred embodiment, M is ruthenium.

$X^1$ and $X^2$ are anionic ligands or polymers, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{20}$ aryl, $C_1$-$C_{20}$ alkoxy, $C_5$-$C_{20}$ aryloxy, $C_3$-$C_{20}$ alkyldiketonate, $C_5$-$C_{20}$ aryldiketonate, $C_2$-$C_{20}$ alkoxycarbonyl, $C_5$-$C_{20}$ aryloxycarbonyl, $C_2$-$C_{20}$ acyl, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl. Optionally, $X^1$ and $X^2$ may be substituted with one or more moieties selected from the group consisting of $C_1$-$C_{10}$ alkyl, $C_1$-$C_{10}$ alkoxy, aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, $X^1$ and $X^2$ are each chloride. The complex may also be attached to a solid support, such as to a polymeric substrate, and this attachment may be effected by means of $X^1$ and/or $X^2$, in which case $X^1$ and/or $X^2$ is a polymer.

$R^1$ is selected from the group consisting of hydrogen, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.), and substituted heteroatom-containing hydrocarbyl (e.g., substituted heteroatom-containing alkyl, alkenyl, alkynyl, aryl, aralkyl, alkaryl, etc.), and carboxyl, and $R^2$ is selected from the group consisting of hydrogen, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.), and substituted heteroatom-containing hydrocarbyl (e.g., substituted heteroatom-containing alkyl, alkenyl, alkynyl, aryl, aralkyl, alkaryl, etc.). $R^1$ and $R^2$ may also be linked to form a cyclic group, which may be aliphatic or aromatic, and may contain substituents and/or heteroatoms. Generally, such a cyclic group will contain 4 to 12, preferably 5 to 8, ring atoms.

In preferred catalysts, the $R^1$ substituent is hydrogen and the $R^2$ substituent is selected from the group consisting of $C_1$-$C_{20}$ alkyl, $C_2$-$C_{20}$ alkenyl, and aryl. More preferably, $R^2$ is phenyl, vinyl, methyl, isopropyl, or t-butyl, optionally substituted with one or more moieties selected from the group consisting of $C_1$-$C_6$ alkyl, $C_1$-$C_6$ alkoxy, phenyl, and a functional group Fn. Still more preferably, $R^2$ is phenyl or vinyl substituted with one or more moieties selected from the group consisting of methyl, ethyl, chloro, bromo, iodo fluoro, nitro, dimethylamino, methyl, methoxy, and phenyl. In the most preferred embodiments, the $R^2$ substituent is phenyl or $-CH=C(CH_3)_2$.

L is a neutral electron donor ligand, and may or may not be linked to $R^2$. Examples of suitable L moieties include, without limitation, phosphine, sulfonated phosphine, phosphite, phosphinite, phosphonite, arsine, stibine, ether (including cyclic ethers), amine, amide, imine, sulfoxide, carboxyl, nitrosyl, pyridine, substituted pyridine (e.g., halogenated pyridine), imidazole, substituted imidazole (e.g., halogenated imidazole), pyrazine (e.g., substituted pyrazine), and thioether. In more preferred embodiments, L is a phosphine of the formula $PR^5R^6R^7$, where $R^5$, $R^6$, and $R^7$ are each independently aryl or $C_1$-$C_{10}$ alkyl, particularly primary alkyl, secondary alkyl or cycloalkyl. In the most preferred embodiments, L is selected from the group consisting of $-P(cyclohexyl)_3$, $-P(cyclopentyl)_3$, $-P(isopropyl)_3$, $-P(phenyl)_3$, $-P(phenyl)_2(R^7)$ and $-P(phenyl)(R^7)_2$, in which $R^7$ is alkyl, typically lower alkyl. Also preferred are weaker ligands such as the nitrogen-containing heterocycles, which enhance catalytic activity presumably because of the requirement that the L ligand dissociate for initiation to occur.

Examples of complexes wherein L and $R^2$ are linked include the following:

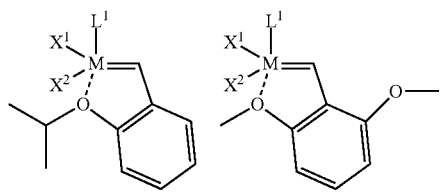

-continued

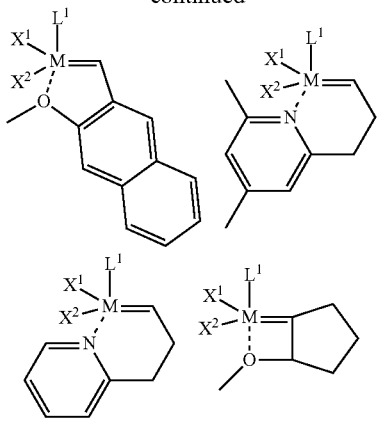

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y and z are independently zero or 1, meaning that each linker is optional. Preferably, w, x, y and z are all zero.

$R^3$, $R^{3A}$, $R^4$, and $R^{4A}$ are independently selected from the group consisting of hydrogen, hydrocarbyl, substituted hydrocarbyl, heteroatom-containing hydrocarbyl, and substituted heteroatom-containing hydrocarbyl, wherein $R^{3A}$ and $R^{4A}$ may be linked to form a cyclic group.

It should be emphasized that any two or more (typically two, three or four) of $X^1$, $X^2$, L, $R^1$, $R^2$, $R^3$, $R^{3A}$, $R^4$, and $R^{4A}$ can be taken together to form a chelating multidentate ligand, as disclosed, for example, in U.S. Pat. No. 5,312,940 to Grubbs et al. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As(Ph)$_2$ CH$_2$CH$_2$As(Ph$_2$)-, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$— and —OC(CH$_3$)$_2$(CH$_3$)$_2$CO—. Preferred bidentate ligands are —P(Ph)$_2$ CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, L, $R^1$, $R^2$, $R^3$, $R^{3A}$, $R^4$, and $R^{4A}$ (e.g., X, L, and any one of $R^3$, $R^{3A}$, $R^4$, and $R^{4A}$) are taken together to be cyclopentadienyl, indenyl or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halogen, $C_1$-$C_6$ alkoxy or with a phenyl group optionally substituted with halogen, $C_1$-$C_6$ alkyl or $C_1$-$C_6$ alkoxy. More preferably, in compounds of this type, X, L, and any one of $R^3$, $R^{3A}$, $R^4$, and $R^{4A}$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, $C_5$-$C_{20}$ aryloxy, each optionally substituted with $C_1$-$C_6$ alkyl, halogen, $C_1$-$C_6$ alkoxy or with a phenyl group optionally substituted with halogen, $C_1$-$C_6$ alkyl or $C_1$-$C_6$ alkoxy. Most preferably, X, L, and any one of $R^3$, $R^{3A}$, $R^4$, and $R^{4A}$ may be taken together to be cyclopentadienyl, optionally substituted with vinyl, hydrogen, Me or Ph. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

In a preferred embodiment, the catalyst has the structure of formula (VIB)

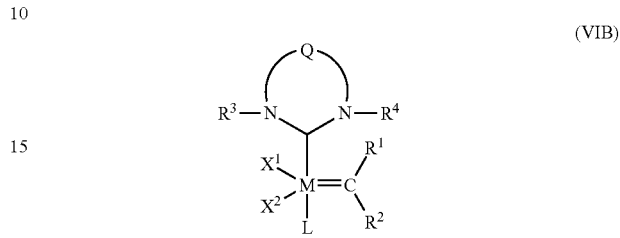

(VIB)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to five cyclic groups. Q is often, although again not necessarily, a two-atom linkage or a three-atom linkage, e.g., —CH$_2$—CH$_2$—, —CH(Ph)—CH(Ph)- where Ph is phenyl; =CR—N=, giving rise to an unsubstituted (when R=H) or substituted (R=other than H) triazolyl group; and —CH$_2$—SiR$_2$—CH$_2$ (where R is H, alkyl, alkoxy, etc.).

In a more preferred embodiment, Q is a two-atom linkage having the structure —CR$^{22}$R$^{22A}$—CR$^{23}$R$^{23A}$— or —CR$^{22}$=CR$^{23}$—, more preferably —CR$^{22}$R$^{22A}$—CR$^{23}$R$^{23A}$—, in which case the complex has the structure of formula (VIC)

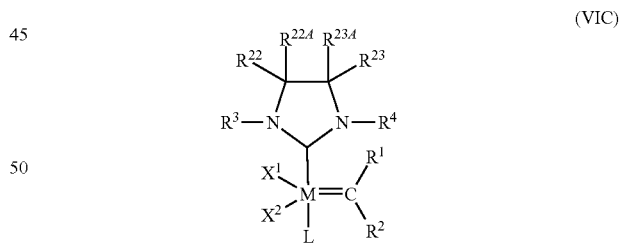

(VIC)

wherein $R^{22}$, $R^{22A}$, $R^{23}$, and $R^{23A}$ are independently selected from the group consisting of hydrogen, hydrocarbyl, substituted hydrocarbyl, heteroatom-containing hydrocarbyl, substituted heteroatom-containing hydrocarbyl, and functional groups (i.e., Fn, as defined previously), e.g., $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, arylthio, $C_1$-$C_{20}$ alkylsulfonyl, and $C_1$-$C_{20}$ alkylsulfinyl, optionally substituted with one or more moieties selected from the group consisting of $C_1$-$C_{10}$ alkyl, $C_1$-$C_{10}$ alkoxy, aryl, hydroxyl, sulfhydryl, —(CO)—H, halide, and functional groups (Fn, again, as defined previously).

Additionally, $R^{22}$, $R^{22A}$, $R^{23}$, and $R^{23A}$ may be linked to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

Examples of N-heterocyclic carbene ligands incorporated into complex (VIC) thus include, but are not limited to, the following:

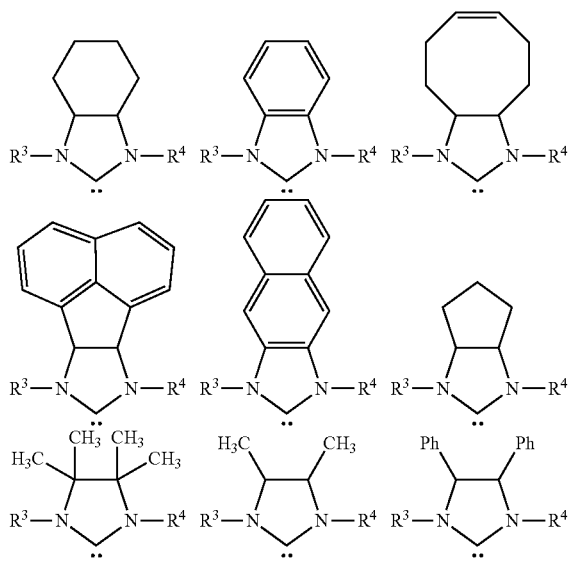

$R^3$ and $R^4$ are preferably aromatic, substituted aromatic, heteroaromatic, substituted heteroaromatic, alicyclic, or substituted alicyclic, composed of from one to about five cyclic groups. When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and have the structure (XII)

(XII)

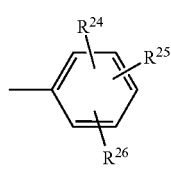

in which $R^{24}$, $R^{25}$, and $R^{26}$ are each independently hydrogen, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{20}$ aryl, substituted $C_5$-$C_{20}$ aryl, $C_5$-$C_{20}$ heteroaryl, $C_5$-$C_{30}$ aralkyl, $C_5$-$C_{30}$ alkaryl, or halogen.

In especially preferred embodiments, $R^{24}$, $R^{25}$, and $R^{26}$ are each independently selected from the group consisting of hydrogen, methyl, ethyl, propyl, isopropyl, hydroxyl, halogen, phenyl, and lower alkyl-substituted phenyl (e.g., dimethylphenyl). In the most preferred embodiments, $R^{24}$, $R^{25}$, and $R^{26}$ are the same and are each methyl.

When $R^3$ and $R^4$ are alicyclic, they are generally composed of a $C_7$-$C_{20}$, preferably a $C_7$-$C_{12}$, alicyclic structure, e.g., diisopinocamphenyl. Complexes formed with such ligands are exemplified by the complex containing the diisopinocamphenyl-substituted ligand shown in structural formula (XIV). In the most preferred embodiments, $R^{24}$, $R^{25}$, and $R^{26}$ are the same and are each methyl. In another preferred embodiment, $R^3$ and $R^4$ are each biphenylyl or substituted biphenylyl. Catalysts formed with such ligands are exemplified by the complex containing the 2,4,2',6'-tetramethylbiphenylyl- (i.e., 2,6-dimethyl-3-(2',6'-dimethylphenyl)phenyl) substituted ligand shown below as structural formula (XIII), preparation of which is described in detail in as illustrated in Example 8.

(XIII)

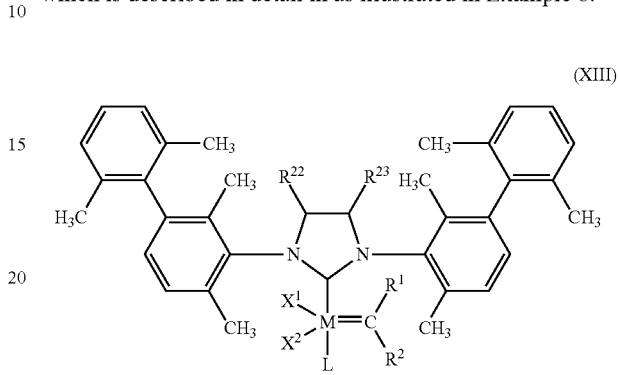

When $R^3$ and $R^4$ are alicyclic, they are generally composed of a $C_7$-$C_0$, preferably a $C_7$-$C_{12}$, alicyclic structure, e.g., diisopinocamphenyl. Complexes formed with such ligands, exemplified by the complex containing the diisopinocamphenyl-substituted ligand shown in structural formula (XIV), are novel compositions of matter and claimed as such herein.

(XIV)

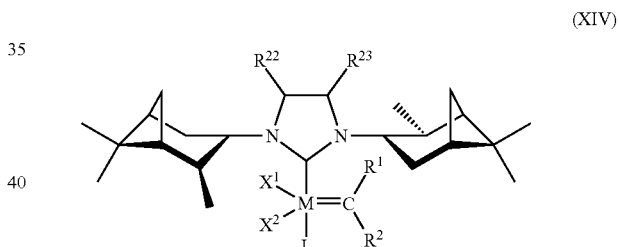

Ligands containing bulky, electron-donating groups such as those illustrated in the complexes of formulae (XIII) and (XIV) provide for very highly active olefin metathesis catalysts. Such catalysts are thus suitable to catalyze reactions for which other, less active catalysts are ineffective, and are also useful in enhancing the stereoselectivity of a catalyzed cross-metathesis reaction.

Examples of more preferred catalysts useful in conjunction with the present methods, then, include, but are not limited to, the following:

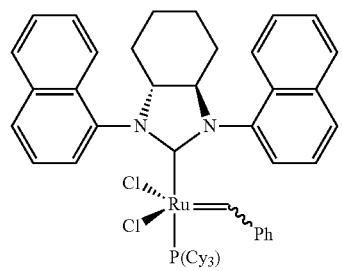

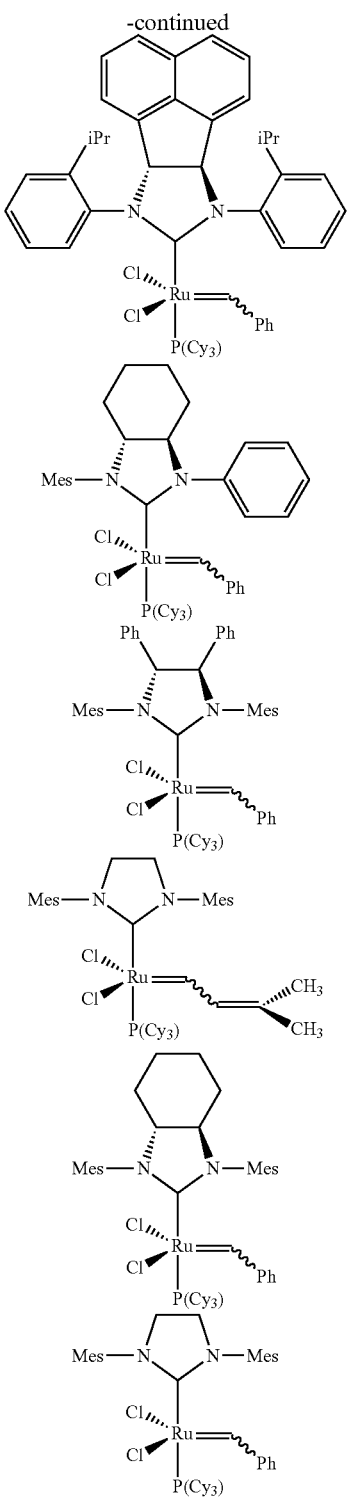

In the above molecular structures, "Mes" represents mesityl (2,4,6-trimethylphenyl), "iPr" is isopropyl, "Ph" is phenyl, and "Cy" is cyclohexyl.

III. Cross-Metathesis of Functionalized and Substituted Olefins:

The present invention, in one embodiment, provides a method for using olefin cross-metathesis to synthesize olefins substituted with functional groups. The reaction is carried out with a functional group-substituted olefinic reactant, and may in fact be carried out with two such functionalized olefins as cross-metathesis reactants. The reaction is catalyzed using a transition metal carbene complex as described in part (II) of this section, and involves reaction between a first olefinic reactant substituted with one or more functional groups, and a second olefinic reactant that may or may not be substituted. With respect to the first olefinic reactant, the functional groups may or may not be in protected form (e.g., a hydroxyl group may be protected as an acyloxy or benzyloxy group). More specifically, the first olefinic reactant has the structure of formula (VIII)

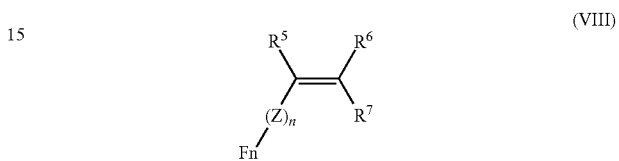

(VIII)

wherein:

Fn is a functional group such as phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, carbamoyl, epoxy, styrenyl, silyl, silyloxy, silanyl, siloxazanyl, boronato, or boryl, or a metal-containing or metalloid-containing group (wherein the metal may be, for example, Sn or Ge);

n is zero or 1;

Z is a hydrocarbylene or a substituted and/or heteroatom-containing hydrocarbylene linking group slinking group such as an alkylene, substituted alkylene, heteroalkylene, substituted heteroalkene, arylene, substituted arylene, heteroarylene, or substituted heteroarylene linkage; and $R^5$, $R^6$, and $R^7$ are independently selected from the group consisting of hydrogen, —(Z)$_n$-Fn, hydrocarbyl, substituted hydrocarbyl, heteroatom-containing hydrocarbyl, and substituted heteroatom-containing hydrocarbyl, and, if substituted hydrocarbyl or substituted heteroatom-containing hydrocarbyl, one or more substituents may be —(Z)$_n$-Fn.

The functional group will generally not be directly bound to the olefinic carbon through a heteroatom containing one or more lone pairs of electrons, e.g., an oxygen, sulfur, nitrogen or phosphorus atom, or through an electron-rich metal or metalloid such as Ge, Sn, As, Sb, Se, Te, etc. With such functional groups, there will normally be an intervening linkage Z, i.e., n is 1.

The second olefinic reactant has a molecular structure given by $R^{18}R^{19}C=CR^{20}R^{21}$ wherein $R^{18}$, $R^{19}$, $R^{20}$, and $R^{21}$ may be hydrogen, hydrocarbyl, substituted hydrocarbyl, heteroatom-containing hydrocarbyl, substituted heteroatom-containing hydrocarbyl, or —(Z)$_n$-Fn, wherein n, Z and Fn are as defined earlier.

In a preferred embodiment, with respect to the first reactant, $R^5$ and at least one of $R^6$ and $R^7$ is hydrogen, Fn is a phosphonate, and Z is lower alkylene, and in a most preferred embodiment, $R^5$, $R^6$ and $R^7$ are hydrogen, and Z is methylene, such that the first olefinic reactant is a vinylphosphonate having the structure of formula (XII)

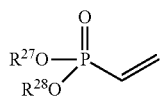

(XV)

when n is zero, and an allylphosphonate having the structure of formula (XIII)

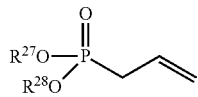

(XVI)

when n is 1. In formulae (XV) and (XVI), $R^{27}$ and $R^{28}$ are hydrocarbyl, preferably lower hydrocarbyl, and most preferably are lower alkyl such as methyl or ethyl.

With respect to the second reactant, it is preferred that $R^{18}$, $R^{19}$, and $R^{20}$ are hydrogen, such that reactant has the structure $H_2C=C(H)R^{21}$.

The capability of the methods of the invention with respect to such reactants are illustrated by a series of experiments summarized in the following tables, using the ruthenium catalyst (V)

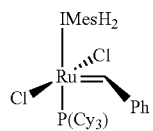

(V)

in which IMesH$_2$ is as defined previously, Cy is cyclohexyl, and Ph is phenyl.

Terminal olefins were reacted with commercially available diethyl vinylphosphonate as described in Example 4. As may be seen in Table 1, cross-metathesis with an olefinic ester resulted in a 95% yield of product, almost exclusively as the (E) isomer (Table 1, Entry 1). No dimerization of the vinylphosphonate was detected by $^1$H-NMR, allowing for selective cross-metathesis. Alkyl halide (Entry 2) and unprotected aldehyde functionalities (Entry 3) were well tolerated with the ruthenium catalyst (V). Allyl benzene also gave the desired metathesis product, without olefin isomerization (Entry 4). The reaction also gave good yields with a variety of styrenes, which were converted to (E)-cinnamylphosphonates in high yield (Table 1, Entry 5).

TABLE 1

[Reaction scheme: EtO-P(=O)(OEt)-CH=CH$_2$ + CH$_2$=CH-R, V (5 mol %), (1.5 eq.), CH$_2$Cl$_2$, 40° C., 12 hr → EtO-P(=O)(OEt)-CH=CH-R]

| Entry | Cross Metathesis Partner | Product | Isolated Yield[a] |
|---|---|---|---|
| 1 | CH$_2$=CH-(CH$_2$)$_3$-OAc | EtO-P(=O)(OEt)-CH=CH-(CH$_2$)$_3$-OAc | 95% |
| 2 | CH$_2$=CH-CH$_2$-Br | EtO-P(=O)(OEt)-CH=CH-CH$_2$-Br | 82% |
| 3 | CH$_2$=CH-(CH$_2$)$_7$-CHO | EtO-P(=O)(OEt)-CH=CH-(CH$_2$)$_7$-CHO | 77% |
| 4 | CH$_2$=CH-CH$_2$-Ph | EtO-P(=O)(OEt)-CH=CH-CH$_2$-Ph | 90% |
| 5 | CH$_2$=CH-C$_6$H$_4$-R | EtO-P(=O)(OEt)-CH=CH-C$_6$H$_4$-R | 97% R = H; 97% R = 4-OMe; 93% R = 4-Br; 77% R = 2,4-(CH$_3$)$_2$ |

[a] >20:1 E/Z as determined by $^1$H-NMR

Second, diethylallylphosphonate was investigated as a cross-metathesis partner. As indicated by the data in Table 2, allylphosphonates are viable cross-metathesis partners using the present method, providing enhanced cross-metathesis ratios relative to the predicted statistical mixture.

TABLE 2

[Reaction scheme: EtO-P(=O)(OEt)-CH$_2$-CH=CH$_2$ + CH$_2$=CH-R, V (mol %), (2.0 eq.), CH$_2$Cl$_2$, 40° C., 12 hr → EtO-P(=O)(OEt)-CH$_2$-CH=CH-R]

| Entry | Metathesis Partner | Product | Isolated Yield | E/Z ratio[a] |
|---|---|---|---|---|
| 1 | CH$_2$=CH-C$_6$H$_5$ | EtO-P(=O)(OEt)-CH$_2$-CH=CH-C$_6$H$_5$ | 70% | >20:1 |

TABLE 2-continued

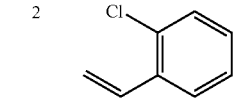

| Entry | Metathesis Partner | Product | Isolated Yield | E/Z ratio[a] |
|---|---|---|---|---|
| 2 | 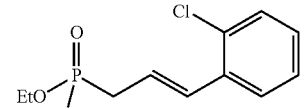 | 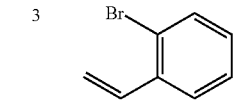 | 93% | >20:1 |
| 3 | 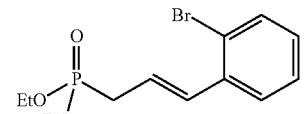 | 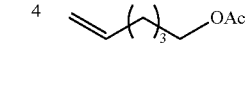 | 73% | >20:1 |
| 4 | 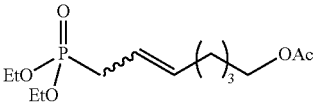 | 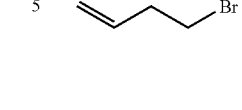 | 74% | 5.4:1 |
| 5 | 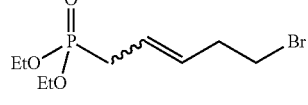 | 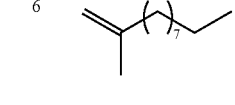 | 85% | 3.5:1 |
| 6 | 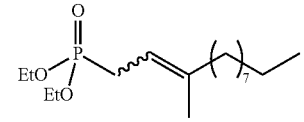 | | 90% | 2.5:1 |

[a]Determined by $^1$H-NMR

In addition, some sterically challenging styrenes proved to be excellent CM partners (Table 2, Entry 2 and 3), providing the E-isomer exclusively. A trisubstituted olefin is also formed in excellent yield with modest stereoselectivity (Table 2, Entry 6). All of the reaction products were easily separated from their respective homodimers by column chromatography.

As noted above, the functional group Fn is not necessarily phosphonate. A significant advantage of the present methodology is that the olefinic reactants can be substituted with one or more of a host of functional groups, even if those functional groups are potential ligands for the catalyst.

For example, catalyst (V) has been used to effect cross-metathesis reactions using allylboronates as starting materials. Such reactions are quite useful in the stereoselective synthesis of homoallylic alcohols. Prior to the present invention, the accessibility of functionalized allyl boron reagents was quite limited, and such complexes are traditionally prepared by allylmetal addition to haloboranes or hydroboration of 1,3-dienes, methods that can be incompatible with complex substrates and/or many desired functional groups. The present invention, however, enables a one pot cross-metathesis/allylboration reaction that affords densely functionalized homoallylic alcohols, as illustrated using pinacol allyl boronate according to the following scheme:

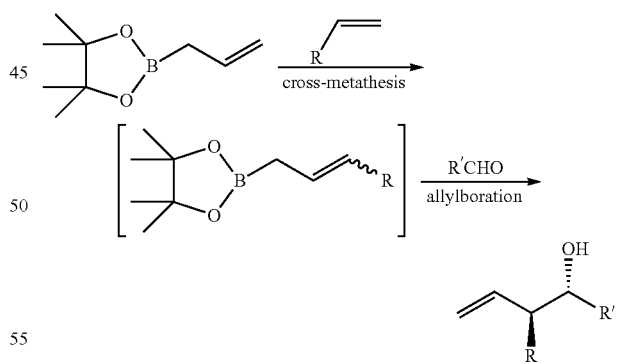

The general procedures for carrying out such reactions are described in detail in Example 9. The effects of varying the catalyst and the relative stoichiometries of components of the cross-metathesis/allylation reaction were explored using (Z)-1,4-diacetoxy-2-butene and benzaldehyde (Table 3). As may be seen, E allylboronates afforded anti products with high diastereoselectivity, and the catalyst of the invention, complex (V), was more E selective than the bis-tricyclohexylphosphine ruthenium alkylidene complex (II), indicating that catalyst (V) provides the homoallylic product with greater anti selectivity. In fact, using the complex of the invention, catalyst loading could be reduced to 2 mol % (Table 3, entry 3) without effecting the yield or diastereoselectivity. The fact that the homoallylic alcohol was formed in 57% yield using a stoichiometric cross partner (Table 3, entry 4), greater than is expected statistically (50%), indicates that the asymmetrically terminated product was favored over symmetrical dimers.

TABLE 3

| entry | eq of cross partner | eq of benzaldehyde | catalyst (mol %) | yield (%) | anti/syn |
|---|---|---|---|---|---|
| 1 | 3 | 1.5 | II (5) | 32 | 1.8/1 |
| 2 | 3 | 1.5 | V (5) | 75 | 4.5/1 |
| 3 | 3 | 1.5 | V (2) | 75 | 4.5/1 |
| 4 | 0.5 | 1.5 | V (5) | 57 | 4.7/1 |
| 5 | 3 | 0.75 | V (5) | 75 | 4.5/1 |

A number of experiments, summarized in Table 4, were carried out in which the aforementioned reaction was used to generate homoallylic alcohols with protected hydroxymethyl, protected aldehyde, and halomethyl side chains from pinacol allyl boronate.

TABLE 4

| entry | cross partner | mol % of V | yield (%) | anti/syn | product |
|---|---|---|---|---|---|
| 1 | TBSO-/=\-OTBS | 5 | 44-67 | 4/1 | 2 |
| 2 | BnO-/=\-OBn | 5<br>2 | 60<br>63 | 4.7/1<br>3.2/1 | 3 |
| 3 | vinyl dioxolane | 5<br>2 | 68<br>69 | >20/1<br>>20/1 | 4 |
| 4 | Br-/=\-Br | 5<br>2 | 73<br>72 | 3.8/1<br>3.6/1 | 5 |
| 5 | Cl-/=\-Cl | 5<br>2 | 78<br>79 | 4.9/1<br>4.6/1 | 6 |

As may be seen in entries 1 and 2, silyl and benzyl allylic ethers were efficiently transformed to the corresponding homoallylic alcohols 2 and 3, respectively, indicating that the methodology enables facile tuning of the olefinic substrate to conform to preexisting protecting group strategies. 2-Vinyl-1,3-dioxolane was effectively converted into alcohol 4 in 69% yield as a single diastereomer (entry 3), indicating that an increase in steric bulk at the allylic carbon atom favors the formation of trans olefins. The present method is also effective in achieving incorporation of a halomethyl group directly by allylboration, a reaction that has not been achieved previously. The bromomethyl (entry 4) and chloromethyl (entry 5) allylation products, 5 and 6 respectively, were synthesized in good yields from the corresponding 1,4-dihalo-2-butenes. The present method thus enables a one-step, one-pot synthesis of halogenated targets that would require several steps to prepare by traditional methods.

As another example, catalyst (V) has been used to prepare secondary allylic alcohols from other protected or unprotected secondary allylic reactants. Examples of such reactions are summarized in Table 5.

In addition, catalyst (V) has been used to dimerize the allylic sulfide 3-methylsulfanyl-propene according to the following scheme:

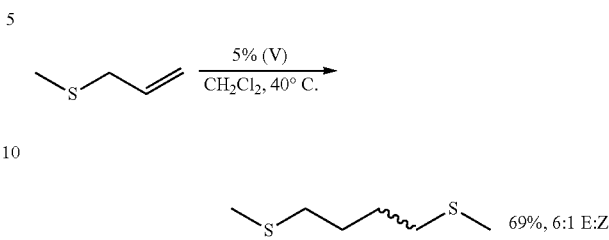

As additional examples, complex (V) has been used to catalyze cross-metathesis reactions with other functionalized olefins, as described in Example 6 and as indicated in Table 6:

TABLE 5

| Allylic Substit. Olefin | Cross Partner | Equiv. | Product | Isolated Yield (%) | E/Z ratio |
|---|---|---|---|---|---|
| HO⌇ | ⌇OAc | 2.0 eq. | HO⌇⌇OAc | 92 | 13:1 |
| HO⌇ | ⌇OEt (acrylate) | 2.0 eq. | HO⌇⌇OEt | 88 | >20:1 |
| BzO⌇ | AcO⌇⌇OAc | 2.0 eq. | BzO⌇⌇OAc | 38 | 18:1 |
| BzO⌇ | ⌇OAc | 2.0 eq. | BzO⌇⌇OAc | 82 | 11:1 |
| TBDPSO⌇ | ⌇OAc | 0.5 eq. | TBDPSO⌇⌇OAc | 53 | 6.7:1 |
| TBDPSO⌇ | ⌇OEt (acrylate) | 0.5 eq. | TBDPSO⌇⌇OEt | 61 | >20:1 |
| dioxolane-vinyl | ⌇OAc | 1.5 eq. | dioxolane⌇⌇OAc | 60 | 6:1 |

TABLE 6

| Entry | | |
|---|---|---|
| 1 | (reaction scheme) | 4a R = C₆H₅ 80%, >95:5 E:Z<br>4b R = C₆H₁₃ 42%, 13:1 E:Z |
| 2 | (reaction scheme) | 71%, >95:5 E:Z |
| 3 | (reaction scheme) | 63%, >95:5 E:Z |
| 4 | (reaction scheme) | 90%, >95:5 E:Z |
| 5 | (reaction scheme) | 87%, >95:5 E:Z |
| 6 | (reaction scheme) | 63%, 3.3:1 E:Z |

As may be seen above, the present method is applicable not only to dimerization of functionalized allylic olefins, but extends to catalytic reaction of such compounds as substrates for cross-metathesis, regardless of the oxidation state of a particular atom in the functional group (e.g., phosphorus-containing functional groups in the form of phosphines, protected phosphines, and phosphonates) or the nature of the functional group (e.g., the reaction proceeds with an allyl amine as well). This versatility is further evidenced by applicants' use of (V) as a catalyst for the preparation of oxazolylphenols as illustrated below:

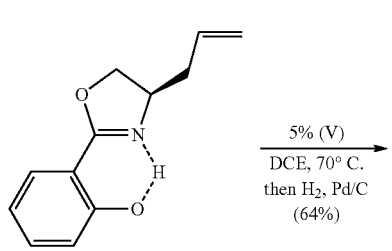

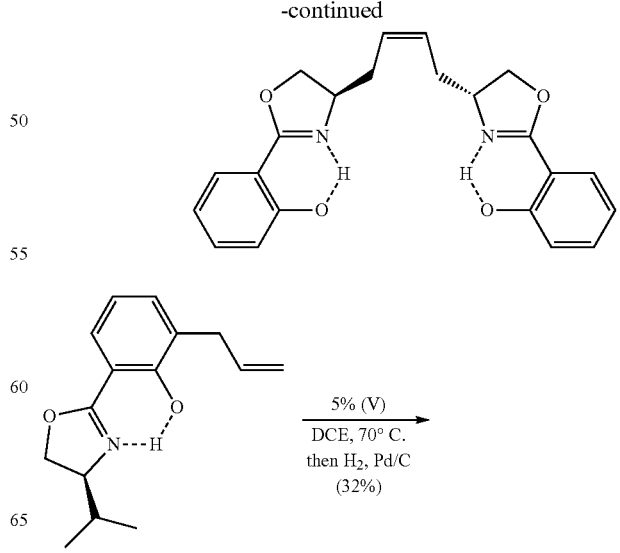

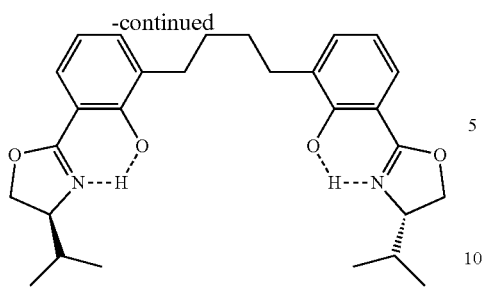

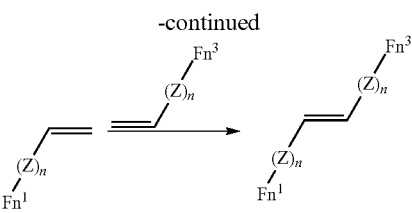

In another aspect of the invention, the versatility of the present methodology is applied to create functional diversity, i.e., to create a plurality of different olefinic products from a single olefinic reactant. This is carried out by conducting a plurality of olefin metathesis reactions each employing a common first olefinic reactant but a different second olefinic reactant. In this way, a plurality of analogs is provided sharing some structural commonality but having a distinguishing feature. As each olefinic reactant may be substituted with functional groups, cross-metathesis products result that contain those groups, thus providing the option of further derivatization. This can be illustrated by reference to the following schemes:

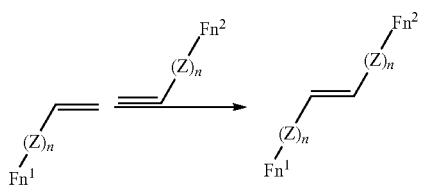

In the above olefins, n and Z are as defined previously, and $Fn^1$, $Fn^2$, $Fn^3$, and $Fn^4$ are as defined for Fn or may include other functional groups, e.g., carboxylate, alkoxy, etc. The olefinic reactants may be further substituted on the olefinic carbon atoms with additional —$(Z)_n$-Fn groups, or with other moieties such as $R^5$, $R^6$, and $R^7$, defined above with respect to the olefins of formula (VIII).

As a specific example, a family of related potential oxazolylphenol ligands was prepared by cross-metathesis of a single olefinic reactant with a plurality of different second olefinic reactants, again using complex (V) as catalyst, as illustrated below:

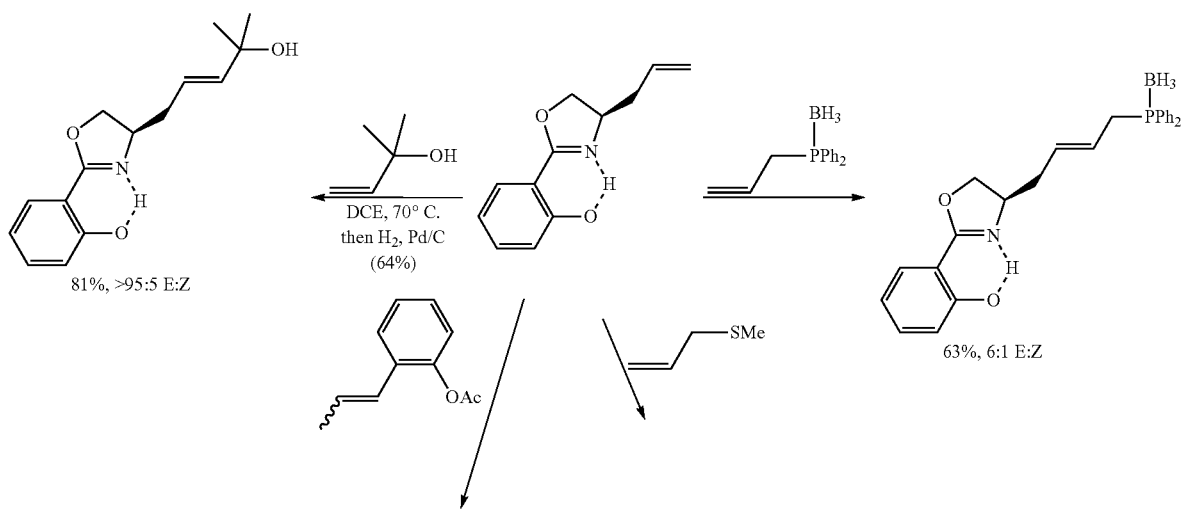

-continued

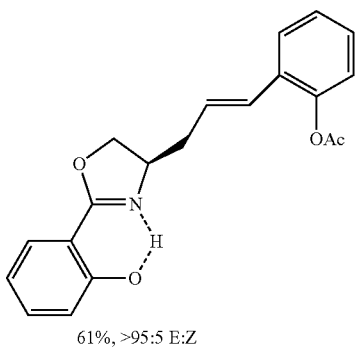

61%, >95:5 E:Z

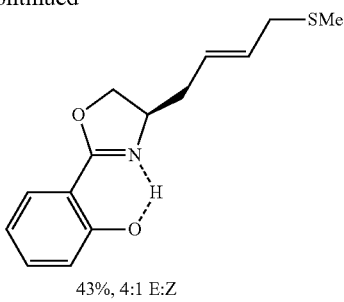

43%, 4:1 E:Z

It will be appreciated that the capability of the invention in this regard enables the generation of diverse libraries of related but structurally distinct compounds, which may then be screened using any of various processes to ascertain utility, e.g., as potential ligands, reactants, biologically active agents, and the like. The method may be generally characterized as a process for generating a plurality of structurally diverse functionalized olefins from a common olefinic reactant via a cross-metathesis reaction, the method involving the following steps:

(a) contacting a functionalized olefinic substrate with a first olefinic reactant in the presence of a catalyst composed of a Group 8 transition metal alkylidene complex containing an N-heterocyclic carbene ligand, under conditions and for a time period effective to allow cross-metathesis to occur;

(b) in a separate reaction, contacting the first olefinic reactant with a second olefinic reactant having a molecular structure that is different from that of the first olefinic reactant, in the presence of the Group 8 transition metal alkylidene complex, under conditions and for a time period effective to allow cross-metathesis to occur; and (c) optionally repeating step (b) with a plurality of olefinic reactants each having a different molecular structure.

In another embodiment, the present invention provides a straightforward method for carrying out an olefin cross-metathesis reaction using an α-halogenated olefin in order to provide a directly halogenated olefinic product. In this embodiment, the catalyst used may be the complex of formula (VIB), or it may be an alternative complex of formula (VI) wherein $L^1$ is a neutral electron donor other than an N-heterocyclic carbene. For example, the catalyst may be a bis(phosphine), in which case both L and $L^1$ of formula (VI) are phosphine ligands such as triphenylphosphine. At least one of the olefinic reactants has the structure of formula (IX)

(IX)

wherein $X^3$ is halo, and $R^8$, $R^9$, and $R^{10}$ are independently selected from the group consisting of hydrogen, halo, hydrocarbyl, substituted hydrocarbyl, heteroatom-containing hydrocarbyl, substituted heteroatom-containing hydrocarbyl, and $—(Z)_n$-Fn where n, Z and Fn are as defined previously with respect to formula (VIII). The second olefinic reactant has the same structure, or the structure $R^{18}R^{19}C=CR^{20}R^{21}$ wherein $R^{18}$, $R^{19}$, $R^{20}$, and $R^{21}$ are as defined previously.

The following schemes exemplify cross-metathesis reactions of this type:

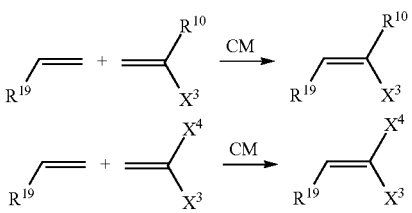

The reaction is straightforward and provides a facile method for obtaining an α-halogenated olefin product.

For example, using the procedures described in Example 5, an olefin metathesis catalyst $(L)(L^1)X^1X^2Ru=CR^1R^2$ such as $(H_2IMes)(PCy_3)Cl_2Ru=CHPh$ reacts with 1,1-difluoroethylene to yield the corresponding methylidene $(H_2IMes)(PCy_3)Cl_2Ru=CH_2$ and difluorocarbene $(H_2IMes)(PCy_3)Cl_2Ru=CF_2$ complexes. At elevated temperatures, greater than 98% of the difluorocarbene complex forms, and it can be isolated in pure form by column chromatography. Although this reaction is not catalytic, the $H_2C=CF_2$ double bond is cleaved in a metathesis fashion, and as such, it is the first example of metathesis involving a directly halide-substituted olefin. In addition, it should be emphasized that $(H_2IMes)(PCy_3)Cl_2Ru=CF_2$ is active for subsequent metathesis reactions, such as the ring-closing metathesis of diethyl diallylmalonate and the ring-opening metathesis polymerization of norbornene derivatives. The activity of $(H_2IMes)(PCy_3)Cl_2Ru=CF_2$ can be enhanced by the addition of HCl or CuCl, which aid in the dissociation of $PCy_3$ from the metal center. The bis(pyridine) derivative of the catalyst, $(H_2IMes)(py)_2Cl_2Ru=CF_2$, is somewhat more active for subsequent metathesis reactions than the $PCy_3$ complex, presumably because the pyridine ligands are less basic and thus more labile. Likewise, the bis(phosphine) olefin metathesis catalyst $(PCy_3)_2Cl_2Ru=CHPh$ reacts with 1,1-difluoroethylene to yield the corresponding methylidene $(PCy_3)_2Cl_2Ru=CH_2$ and difluorocarbene $(PCy_3)_2Cl_2Ru=CF_2$ complexes.

In a further embodiment, a method is provided for synthesizing substituted olefins, particularly geminal disubstituted olefins, 1,1,2-trisubstituted olefins and quaternary allylic olefins, wherein the method comprises using the complex of formula (VI) to catalyze a cross-metathesis reaction between a geminal disubstituted olefin, a 1,1,2-trisubstituted olefin, or a quaternary allylic olefin, and a second olefin. If it is a geminal disubstituted olefin or a 1,1,2-trisubstituted olefin, the first olefin has the structure (X)

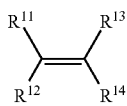

(X)

wherein $R^{11}$, $R^{12}$, $R^{13}$, and $R^{14}$ are selected from the group consisting of hydrogen, halo, hydrocarbyl, substituted hydrocarbyl, heteroatom-containing hydrocarbyl, substituted heteroatom-containing hydrocarbyl, and —$(Z)_n$-Fn where n, Z and Fn are as defined above, with the provisos that $R^{11}$ and $R^{12}$, or $R^{13}$ and $R^{14}$ are other than hydrogen for a geminal disubstituted olefin, and that $R^{11}$, $R^{12}$, and $R^{13}$ are other than hydrogen for a 1,1,2-trisubstituted olefin. If it is a quaternary allylic olefin, the first olefin has the structure (XI)

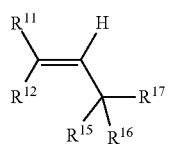

(XI)

wherein $R^{11}$ and $R^{12}$ are as defined previously, and $R^{15}$, $R^{16}$, and $R^{17}$ are nonhydrogen substituents.

In the aforementioned cross-metathesis reaction, the second olefin has a molecular structure given by $R^{18}R^{19}C=CR^{20}R^{21}$ wherein $R^{18}$, $R^{19}$, $R^{20}$, and $R^{21}$ may be hydrogen, hydrocarbyl, substituted hydrocarbyl, heteroatom-containing hydrocarbyl, or substituted heteroatom-containing hydrocarbyl.

Generally, the reaction is carried out with the two olefinic reactants in a mole ratio in the range of about 1:3 to 3:1, at a temperature in the range of about 20° C. to about 40° C., for a time period in the range of about 4 to 16 hours. Typically, about 0.01 to 7.5 mole % catalyst is used. However, the reaction is also viable if there is a large excess of one reactant, such as is the case when one reactant serves as a solvent for the reaction mixture.

Another example of such a reaction is the synthesis of 1,1-dimethyl olefins through a cross-metathesis reaction of α-olefins with isobutylene or 2-methyl-2-butene. The capability of the methods of the invention with respect to such a reaction is illustrated by a series of experiments summarized in Table 7, using 2-methyl-2-butene as the geminal disubstituted olefin and (IMesH$_2$)(PCy$_3$)Cl$_2$Ru=C(H)Ph (complex (V)) as the catalyst.

TABLE 7

| Entry | Terminal α-Olefin | Product | Yield |
|---|---|---|---|
| 1 | allyl-P(O)(OEt)$_2$ | 3-methyl-2-butenyl-P(O)(OEt)$_2$ | 97 |
| 2 | pentenyl-OAc | methylbutenyl-OAc | 97 |
| 3 | 3-nitrostyrene | 3-nitro-β-methylstyrene | 96 |
| 4 | hexenyl-(CH$_2$)$_5$CHO | methylpentenyl-(CH$_2$)$_5$CHO | 91 |
| 5 | allyl-C$_6$F$_5$ | methylbutenyl-C$_6$F$_5$ | 91 |
| 6 | 2-(TBSO)-allylbenzene | 2-(TBSO)-methylbutenylbenzene | 99 |
| 7 | vinyl-CH(OBz)-CH(CH$_3$)$_2$ | methylbutenyl-CH(OBz)-CH(CH$_3$)$_2$ | 80 |
| 8 | acrylate On-Bu | crotonate On-Bu | 83 |

Additional experiments, summarized in Table 8, were carried out using catalyst (V) to generate trisubstituted olefins from symmetrical 1,1-disubstituted olefins as starting materials.

TABLE 8

| Entry | 1,1-Disubstituted Olefin | Temp(° C.) | Metathesis Partner | Product | Isolated Yield |
|---|---|---|---|---|---|
| 1 | isobutylene | 40 | hexenyl-OAc | methyl-hexenyl-OAc | 97 |
| 2 | isobutylene | 40 | (AcO)CH$_2$CH=CHCH$_2$(OAc) | methylbutenyl-OAc | 88 |

TABLE 8-continued

| Entry | 1,1-Disubstituted Olefin | Temp(° C.) | Metathesis Partner | Product | Isolated Yield |
|---|---|---|---|---|---|
| 3 | BzO— / BzO— (methylene diol dibenzoate) | 40 | hexenyl-OAc | BzO-substituted alkene-OAc | 48 |
| 4 | methylenecyclohexane | 40 | hexenyl-OAc | cyclohexylidene-alkyl-OAc | 65 |
| 5 | isobutylene | 40 | diallyl-OBz | bis-prenyl-OBz | 96 |
| 6 | isobutylene | 40 | 4-vinylbiphenyl | prenyl-biphenyl | 42 |
| 7 | isobutylene | 40 | adamantyl acrylate | adamantyl senecioate | 83 |

Further experiments illustrating the versatility of the present methodology were carried out in order to generate 1,2-disubstituted olefins with quaternary allylic carbons using the catalyst (V), the results of which are summarized in Table 9.

TABLE 9

| Entry | Quat. Allylic Olefin | Equiv. | CM Partner | Product | Yield |
|---|---|---|---|---|---|
| 1 | HO-C(Me)₂-CH=CH₂ | 0.5 eq. | acrylate-OBu | HO-C(Me)₂-CH=CH-CO-OBu | 95 |
| 2 | TBSO-C(Me)₂-CH=CH₂ | 2.0 eq. | hexenyl-OAc | TBSO-C(Me)₂-CH=CH-(CH₂)₃-OAc | 97 |
| 3 | TBSO-CH₂-C(OH)(CH₂OTBS)-CH=CH₂ | 0.5 eq. | hexenyl-OAc | TBSO-CH₂-C(OH)(CH₂OTBS)-CH=CH-(CH₂)₃-OAc | 66 |
| 4 | neopentyl-type alkene | 2.0 eq. / 1.0 eq. | hexenyl-OAc | cross product-OAc | 90 / 69 |
| 5 | neopentyl-type alkene | 3 eq. | allylbenzene | cross product with phenyl | 88 |

TABLE 9-continued

| Entry | Quat. Allylic Olefin | Equiv. | CM Partner | Product | Yield |
|---|---|---|---|---|---|
| 6 | | ~50 eq. | AcO/=\OAc | tBu-CH=CH-CH2-OAc type | 93 |
| 7 | | 3 eq. | /=\~~\OAc | | 44 |
| 8 | HO-substituted | 2 eq. | /=\~~\OAc | HO-substituted product | 93 |
| 9 | dioxolane-vinyl | 1 eq. | /=\~~\OAc | dioxolane product with OAc | 95 |
| 10 | dioxolane-vinyl | 2 eq. | =\Ph | dioxolane product with Ph | 71 |

These reactions were stereoselective, resulting in virtually exclusive formation of the trans olefin isomer, as may be seen under the column heading "E/Z Ratio" in the FIGURE. This stereoselectivity is an important feature of the method, insofar as prior to the present invention, there was no general method for controlling the stereoselectivity of newly formed olefins.

In a related embodiment of the invention, a stereoselective method for carrying out an olefin cross-metathesis reaction is provided, wherein the stereochemistry of the olefinic product may be either cis or trans, as desired. The catalyst used has the structure of formula (VIB), wherein the nitrogen atoms of the N-heterocyclic carbene ligand are substituted with bulky substituents, i.e., $R^3$ and $R^4$ are aromatic, substituted aromatic, heteroaromatic, substituted aromatic, alicyclic, or substituted alicyclic. For a stereoselective synthesis that will preferentially result in a cis-1,2-disubstituted olefin, bulky $R^3$ and $R^4$ substituent are preferred, e.g., bicyclic or polycyclic ligands that may or may not be aromatic. If $R^3$ and $R^4$ are aromatic, they are generally composed of two to five aromatic rings that may be fused or linked (e.g., biphenyl or substituted biphenyl), and if $R^3$ and $R^4$ are alicyclic, they are generally composed of a $C_7$-$C_{20}$, preferably a $C_7$-$C_{12}$, alicyclic structure that may or may not be substituted. Representative such $R^3$ and $R^4$ groups thus include the alicyclic groups norbornyl, adamantyl, camphenyl, isobornyl, any of which may be substituted, e.g., with a lower alkyl group (as in diisopinocamphenyl, as shown in the structure of formula (XIV)), and the bicyclic groups biphenylyl and 2',6'-dimethyl-3'-(2'',6''-dimethylphenyl)phenyl (as shown in the structure of formula (XIII)).

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXPERIMENTAL

IMesH$_2$Cl was prepared according to a modified version of the procedure described in Scholl et al. (1999) Org. Lett. 1:953-956 and Jafarpour et al. (2000) Organometallics 19:2055-2057. Unless otherwise specified, all other reagents were purchased from commercial suppliers and used without further purification. All other solvents were purified by passage through a solvent column (containing activated A-2 alumina; see Pangborn et al. (1996) Organometallics 15:1518-1520.). Analytical thin-layer chromatography (TLC) was performed using silica gel 60 F254 precoated plates (0.25 mm thickness) with a fluorescent indicator. Flash column chromatography was performed using silica gel 60 (230-400 mesh) from EM Science. $^1$H, $^{13}$C, and $^{31}$P NMR spectra were obtained on a Varian 300 MHz Fourier Transform spectrometer (300 MHz $^1$H, 75.4 MHz $^{13}$C, 121.4 MHz $^{31}$P). All chemical shift values are given in parts-per million (δ) and are referenced with respect to residual solvent ($^1$H and $^{13}$C) or phosphoric acid ($^{31}$P).

Preparation of IMesH$_2$Cl: IMesH$_2$Cl, used as a starting material in Examples 1 through 3, was synthesized according to the following scheme:

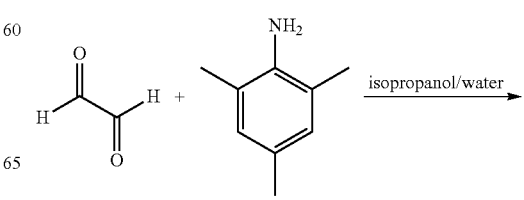

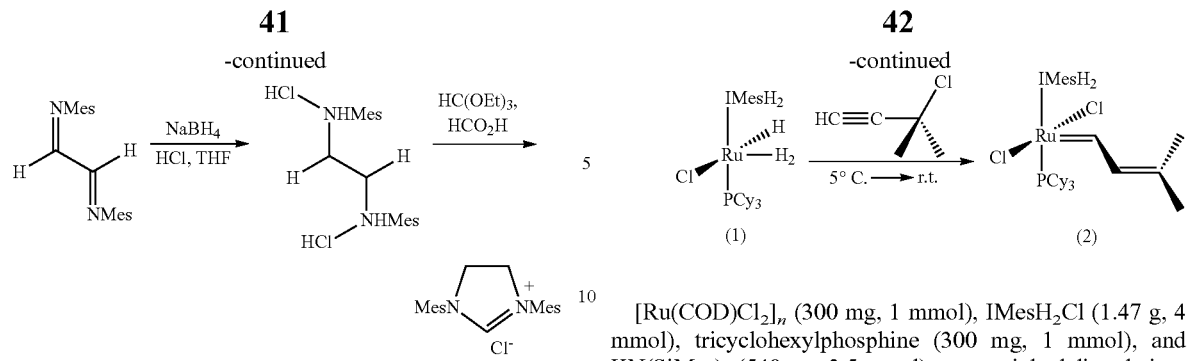

To a solution of glyoxal (9 mL, 79 mmol, 40% wt in H$_2$O) in isopropanol (100 mL) and H$_2$O (200 mL) was added mesitylamine (25 mL, 2.2 eq.) at 0° C. The reaction mixture was stirred while allowing to warm to room temperature. Immediately upon addition of amine, yellow precipitates were formed. After 24 hrs of stirring at ambient temperature, the precipitates were filtered and washed with H$_2$O (1×100 mL) and hexanes (3×100 mL). The yellow precipitates obtained were dried in vacuo to yield the diimine (20.6 g, 89%).

To a solution of diimine (8.0 g, 27.3 mmol) in THF (100 mL) was added NaBH$_4$ (4.24 g, 112.1 mmol) at 0° C. Concentrated HCl (4.5 mL, 2 eq.) was added dropwise over 30 minutes. After the HCl addition, the reaction mixture was stirred at 0° C. for 20 min. Then, 3 M HCl (250 mL) was added carefully to the flask at 0° C. and the mixture was stirred for an additional 1 hr, allowing the temperature to rise to ambient temperature. The resulting white precipitates were filtered and washed with water (200 mL) and 5% acetone-ether (150 mL). The product (9.4 g, 93%) was obtained as a white solid and dried in vacuo. To a suspension of the HCl salt (8.5 g, 23 mmol) in HC(OEt)$_3$ (35 mL, 162 mmol) was added 2 drops of HCO$_2$H (adding about 1 mol %). The reaction mixture was then heated at 120° C. for 5 hr under Ar. Then, the reaction mixture was cooled to an ambient temperature and hexane (200 mL) was added. The mixture was stirred for 1 hr and the white precipitates were filtered, washed with hexane (~200 mL) and dried in vacuo to yield the IMesH$_2$.HCl salt (7.6 g, 96%).

EXAMPLE 1

Representative Procedure for Synthesis of Ruthenium Alkylidene Catalysts

Synthesis of RuCl$_2$(=CH—CH=C(CH$_3$)$_2$)(IMesH$_2$)(PCy$_3$) (complex (2), Scheme 1)

SCHEME 1

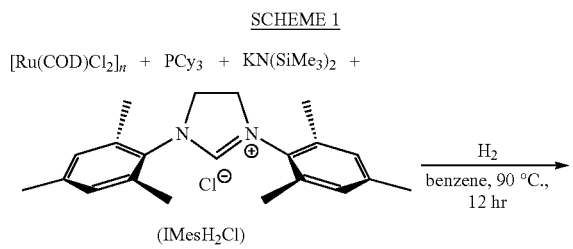

[Ru(COD)Cl$_2$]$_n$ (300 mg, 1 mmol), IMesH$_2$Cl (1.47 g, 4 mmol), tricyclohexylphosphine (300 mg, 1 mmol), and KN(SiMe$_3$)$_2$ (540 mg, 2.5 mmol) were weighed directly into a 600 mL Schlenk tube. The flask was evacuated and filled with dry argon (2×). Degassed benzene (300 mL) was added and the flask was pressurized to 30 psi with H$_2$. The suspension was vigorously stirred for 12 hours at 90° C., yielding a bright yellow solution and white precipitate (1). After cooling the reaction to 5° C., propargyl chloride (0.3 mL, 4 mmol) was slowly added via syringe and the reaction mixture was allowed to warm to room temperature. The resulting brown benzene solution was washed with degassed 1M HCl (2×), degassed brine (2×), filtered through Celite and concentrated in vacuo to afford compound (2) as a brown solid in 90% yield (~95% purity). The brown solid displayed catalytic behavior identical with previously synthesized second-generation catalysts. Analytically pure (2) was obtained by column chromatography on silica gel (degassed 3:1 hexanes/Et$_2$O). $^1$H NMR (CD$_2$Cl$_2$): δ 18.49 (d, J=11.1 Hz, 1H), 7.26 (d, J=10.9 Hz, 1H), 6.97 (s, 2H), 6.77 (s, 2H), 3.92 (m, 4H), 2.58 (s, 6H), 2.37 (s, 6H), 2.29 (s, 3H), 2.23 (s, 3H), 0.88-1.584 (m, 33H), 1.06 (s, 3H), 1.08 (s, 3H). $^{31}$P NMR (CD$_2$Cl$_2$): δ 28.9. The reaction was repeated several times with one or more reaction conditions modified so as to optimize the yield of the product. It was found that the yield could be increased to greater than 95% by reducing the reaction temperature from 90° C. to 80° C.

Analogous ruthenium alkylidene complexes can be prepared using the aforementioned protocol and differently substituted phosphines, alkynes, etc., as indicated in the following two examples.

EXAMPLE 2

Synthesis of RuCl$_2$(=CH—CH=C(CH$_3$)$_2$)(IMesH$_2$)(PPh$_3$) (complex (4), Scheme 2)

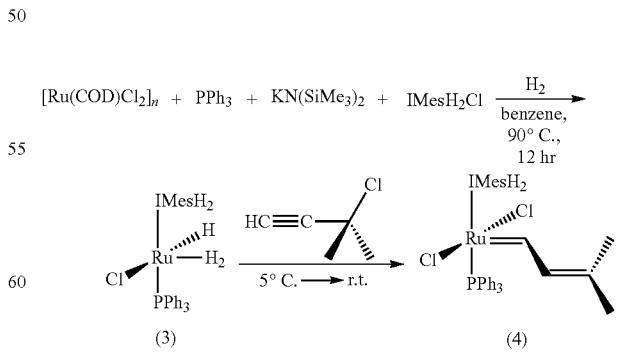

The procedure of Example 2 was employed using [Ru(COD)Cl$_2$]$_n$(300 mg, 1 mmol), IMesH$_2$Cl (0.74 g, 2 mmol), triphenylphosphine (280 mg, 1 mmol), and KN(SiMe$_3$)$_2$ (380 mg, 1.9 mmol), giving 550 mg (68%) of complex (3). $^{31}$P NMR (CD$_2$Cl$_2$): δ 24.0. $^1$H NMR (CD$_2$Cl$_2$): δ 18.49 (d, J=11.1 Hz, 1H).

EXAMPLE 3

Synthesis of RuCl$_2$(=CH—CH-Ph)(IMesH$_2$)(PCy$_3$) (complex (5), Scheme 3)

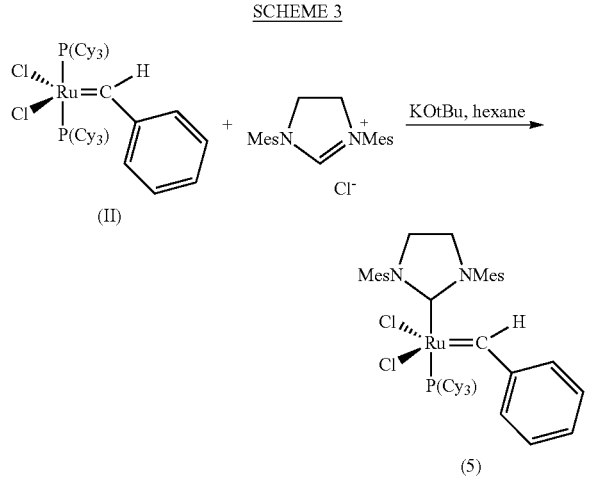

RuCl$_2$(=CHPh)(PCy$_3$)$_s$ (phenylmethylene-bis(tricyclohexylphosphine) ruthenium dichloride, "catalyst (I)") (6.00 g, 7.29 mmol, 1.0 eq.), IMesH$_2$.HCl salt prepared above (2 eq.), and potassium t-butoxide (2 eq.) were placed in a Schlenk flask. 60 mL of anhydrous degassed hexanes (Aldrich SureSeal bottle) were added. A vacuum was applied to further degas the reaction mixture, which was then heated to 60° C. for 24 hours. The suspension changed color from purple to orange-brown over the reaction time. After approximately 24 hr, the mixture was cooled to room temperature, and an excess of 1:1 isopropanol:water (180 mL) was added. The mixture was stirred rapidly in air for 30 min., then filtered using a medium porosity frit, and washed with isopropanol-water (3×100 mL) and hexanes (3×100 mL). The solids were dried in in vacuo, and the yield was approximately 75%. $^1$H NMR (CD$_2$Cl$_2$, 400 MHz) δ 19.16 (s, 1H), 7.37-7.05 (m, 9H), 3.88 (s, 4H), 2.56-0.15 (m, 51H); $^{31}$P NMR (CD$_2$Cl$_2$, 161.9 MHz) δ 31.41; HRMS (FAB) C$_{45}$H$_{65}$Cl$_2$N$_2$PRu [M$^+$] 848.3306, found 848.3286.

EXAMPLE 4

Representative Procedures for Cross-Metathesis Reactions Used to Synthesize Functionalized Olefins Preparation of Olefinic Phosphonates (Tables 1 and 2): Terminal olefin (0.75 mmol) and diethyl vinylphosphonate (Aldrich) or diethyl allylphosphonate (Acros Organics, 0.51 mmol) were added simultaneously via syringe to a stirring solution of (5) (21 mg, 0.026 mmol, 5.2 mol %) in CH$_2$Cl$_2$ (2.5 mL, 0.2M in phosphonate) under a nitrogen atmosphere. The flask was fitted with a condenser and refluxed under nitrogen for 12 hours. The reaction mixture was then reduced in volume to 0.5 mL and purified directly on a silica gel column (2×10 cm), eluting with 1:1 hexane:ethyl acetate to provide cross products as viscous oils.

EXAMPLE 5

Representative Procedures for Synthesis of Directly Halogenated Olefins

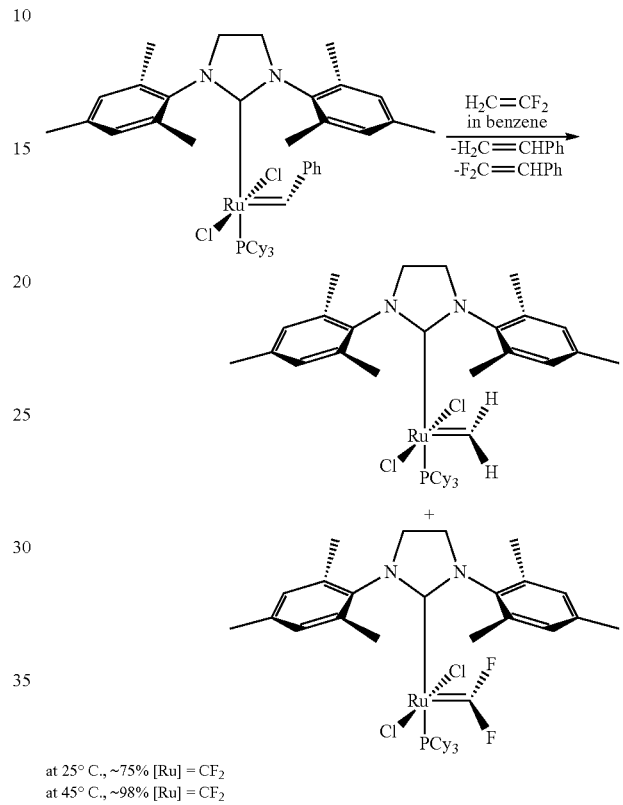

at 25° C., ~75% [Ru] = CF$_2$
at 45° C., ~98% [Ru] = CF$_2$

Synthesis and characterization of [(IMesH$_2$)(PCy$_3$)(Cl)$_2$Ru=CF$_2$]: A solution of 0.32 g (0.37 mmol) [(IMesH$_2$)(PCy$_3$)(Cl)$_2$Ru=CHPh] (5) in dry, degassed benzene (15 mL) in a thick-walled glass ampule was put under ~1.5 atm of 1,1-difluoroethylene. The reaction was heated at 60° C. for 12 hrs, during which time it changed from reddish to brown in color. The solution was then concentrated to 5 mL and purified by column chromatography in air (silica gel, 5:1 pentane/THF). The orange fraction was stripped of solvent and dried under vacuum: yield 0.26 g (86%). $^1$H NMR (499.852 MHz, 25° C., CD$_2$Cl$_2$): δ 1.118 [br, 15H, PCy$_3$], 1.626 [br, 15H, PCy$_3$], 2.248 [s, 3H, p-CH$_3$ of Mes], 2.285 [s, 3H, p-CH$_3$ of Mes], 2.385 [m, 3H, PCy$_3$], 2.480 [s, 6H, o-CH$_3$ of Mes], 2.551 [s, 6H, o-CH$_3$ of Mes], 4.003 [s, 4H, NCH$_2$CH$_2$N], 6.921 [s, 4H, m-H of Mes]. $^{13}$C {$^1$H} NMR (125.705 MHz, 30° C., C$_6$D$_6$): δ 19.44 [s, CH$_3$ of Mes], 20.65 [s, CH$_3$ of Mes], 21.49 [s, CH$_3$ of Mes], 21.50 [s, CH$_3$ of Mes], 26.92 [d, J=1.3 Hz, PCy$_3$], 28.50 [d, J=10 Hz, PCy$_3$], 30.14 [s, PCy$_3$], 33.34 [d, J=18 Hz, PCy$_3$], 51.86 [d, $^4J_{PC}$=2.6 Hz, NCH$_2$CH$_2$N], 52.61 [d, $^4J_{PC}$=3.5 Hz, NCH$_2$CH$_2$N], 127.30 [s, Mes], 128.17 [s, Mes], 129.26 [s, Mes], 129.51 [s, Mes], 130.11 [s, Mes], 130.52 [s, Mes], 134.68 [d, $^4J_{PC}$=0.7 Hz, ipso-C of Mes], 136.85 [s, ipso-C of Mes], 138.91 [s, Mes], 138.93 [s, Mes], 139.03 [s, Mes], 139.67 [s, Mes], 217.23 [d, $^2J_{CP}$=87 Hz, NCN], 218.09 [td, $^2J_{CP}$=12 Hz, $^1J_{CF}$=430 Hz, Ru=CF$_2$]. $^{19}$F NMR (282.192 MHz, 25° C., CD$_2$Cl$_2$): δ 133.74 [d, $^3J_{FP}$=4.5

Hz]. $^{31}$P {$^1$H} NMR (121.392 MHz, 25° C., CD$_2$Cl$_2$): δ 32.15 (t, $^3$ J$_{PF}$=4.4 Hz]. IR (KBr pellet): 1167 and 1172 (ν$_{C-F}$).

When the reaction is performed at room temperature, the product mixture contains approximately 40% methylidene and 60% difluorocarbene, as well as styrene (H$_2$C=CHPh) and β,β-difluorostyrene (F$_2$C=CHPh). The amount of difluorocarbene complex formed increased to greater than 98% when the reaction was carried out at 60° C. instead. In a similar fashion, the bis(phosphine) olefin metathesis catalyst [(PCy$_3$)$_2$Cl$_2$Ru=CHPh] reacts with 1,1-difluoroethylene to yield the corresponding methylidene [(PCy$_3$)$_2$Cl$_2$Ru=CH$_2$] and difluorocarbene [(PCy$_3$)$_2$Cl$_2$Ru=CF$_2$] complexes.

EXAMPLE 6

Representative Procedures for Synthesis of Substituted Allylic Olefins

Allyldiphenylphosphine oxide (53 mg, 0.22 mmol) and catalyst (5) (14 mg, 0.0165 mmol) were weighed directly into a dried 25 mL round bottom flask with a Teflon stirbar. Dry methylene chloride (1.5 mL, 0.3M) and cis-2-butene-1,4-diacetate (TCI) (70 L, 0.44 mmol) were added via syringe under a nitrogen atmosphere. The flask was fitted with a condenser and refluxed under nitrogen for 12 hours. The reaction mixture was then reduced in volume to 0.5 mL and purified directly on a silica gel column (2×10 cm), eluting with 1:1 hexane:ethyl acetate to provide the cross product (62 mg, 90% yield) as viscous oil/semi solid as confirmed by $^1$H and $^{13}$C-NMR.

EXAMPLE 7

Representative Procedures for Synthesis of Trisubstituted and Quaternary Allylic Olefins General procedure for isobutylene CM: To an oven dried, 100 mL Fischer-Porter bottle with Teflon stir bar, ruthenium metathesis catalyst (15.0 mg, 0.018 mmol, 0.01-0.02 equiv.) was added. The bottle was capped with a rubber septum and flushed with dry nitrogen and cooled to −78° C. (or temperature sufficient to freeze substrate). Substrate (0.9-1.9 mmol) was injected into the bottle. Once the substrate was frozen, a pressure regulator was attached to the bottle. The bottle was evacuated and backfilled with dry nitrogen 3 times. Subsequently, isobutylene (5-10 mL, 50-100 equiv.) was condensed into the bottle. The bottle was backfilled to ~2 psi with nitrogen, sealed, and allowed to slowly warm to room temperature, at which time it was transferred to an oil bath at 40° C. After stirring for 12-18 hours, the bottle was removed from the oil bath and allowed to cool to room temperature. The isobutylene was slowly vented off at room temperature until the pressure apparatus could be safely disassembled. The remaining mixture was taken up in organic solvent for subsequent silica gel chromatography and/or spectrographic characterization.

Representative procedure for CM with 2-methyl-2-butene (Table 7, Entry 5): Pw Pentafluoroallylbenzene (225 μL, 1.468 mmol) from Aldrich Chem. Co. and 2-methyl-2-butene (3.2 mL) from Aldrich Chem. Co. were added simultaneously via syringe to a stirring solution of catalyst (5) (12.5 mg, 0.015 mmol, 1.0 mol %) under a nitrogen atmosphere. The reaction mixture was allowed to stir at room temperature for 12 hours, and was then reduced in volume to 0.5 mL and purified directly on a silica gel column (2×10 cm), eluting with 20:1 hexane:ethyl acetate to provide the cross-metathesis product (316 mg, 1.337 mmol, 91% yield) as a viscous oils.

Representative procedure for CM with 3,3-dimethyl-1-butene (Table 8, Entry 6): Cis-2-butene-1,4-diacetate (50 μL, 0.3168 mmol) from TCI America and 3,3-dimethyl-1-butene (3.2 mL, 0.15M) from Aldrich Chem. Co. were added simultaneously via syringe to a stirring solution of catalyst (5) (10 mg, 0.012 mmol, 3.7 mol %) under a nitrogen atmosphere. The flask was allowed to stir at room temperature for 12 hours. The reaction mixture was then reduced in volume to 0.5 mL and purified directly on a silica gel column (2×10 cm), eluting with 50:1 hexane:ethyl acetate to provide the cross-metathesis product (92 mg, 0.5891 mmol, 93% yield) as a viscous oils.

Representative 40° C. procedure with 3,3-dimethyl-1-hexene (Table 8, Entry 5): Allylbenzene (40 μL, 0.30 mmol) from Aldrich Chem. Co. and 3,3-dimethyl-1-hexene (140 μL, 0.90 mmol, 3 equiv.) from Aldrich Chem. Co were added simultaneously via syringe to a stirring solution of catalyst (5) (20 mg, 0.024 mmol, 7.8 mol %) in CH$_2$Cl$_2$ (2.0 mL, 0.15M in allylbenzene) under a nitrogen atmosphere. The flask was fitted with a condenser and refluxed under nitrogen for 12 hours at 40 C. The reaction mixture was then reduced in volume to 0.5 mL and purified directly on a silica gel column (2×10 cm), eluting with 20:1 hexane:ethyl acetate to provide the cross product (54 mg, 0.27 mmol, 88% yield) as a viscous oils.

EXAMPLE 8

Representative Procedures for Synthesis of Cis-1,2-Disubstituted Olefins (a) General considerations: All manipulations were performed using a combination of glovebox, high vacuum, and Schlenk techniques under a nitrogen atmosphere, unless otherwise specified. Solvents were dried and degassed by standard procedures. $^1$H and $^{13}$C NMR spectra were measured on a Varian 300 or an Inova 500 spectrometer. Chemical shifts are reported in ppm relative to SiMe$_4$ (δ=0) and were referenced internally with respect to the protio solvent impurity (δ=5.32 for CDHCl$_2$) and the $^{13}$C resonances (δ=54.00 for CD$_2$Cl$_2$). Coupling constants are in hertz. The silica gel used for the purification of organometallic complexes was obtained from TSI Scientific, Cambridge, Mass. (60 Å, pH 6.5-7.0).

(b) Preparation of representative catalysts useful for stereoselective synthesis of cis-1,2-disubstituted olefins: The ligand precursors 1,3-(+)diisopinocamphenyl-4,5-dihydroimidazolium tetrafluoroborate salt [IPCimid(H)][BF$_4$] and 1,3-bis[2',6'-dimethyl-3'-(2",6"-dimethylphenyl)phenyl]-4,5-dihydroimidazolium chloride salt were prepared by analogy to the method of Kaloustian et al. (see Saba et al. (1991) Tet. Lett. 32:5031-34).

(b-i) In a nitrogen-filled glovebox, a large Schlenk flask was charged with 0.475 g [IPCimid(H)][BF$_4$] (1.120 mmol), 0.131 g potassium tert-butoxide (1.120 mmol), and 30 mL anhydrous, degassed benzene. This mixture was stirred at room temperature for 6 hrs. Then, a solution of 0.400 g [(PCy$_3$)$_2$(Cl)$_2$ Ru=CHPh] (0.486 mmol) in 15 mL benzene was added, and the reaction was stirred for 30 min at room temperature, during which time the mixture changed from purple to brown. The reaction was concentrated to a third of its original volume under vacuum and transferred to a silica gel column (1.5×16"). The product was quickly eluted with 5:1 heptane:ether. The second, brown band was collected and stripped of solvent. The oily residue that remained was redissolved in a minimum amount of benzene and lyophylized to yield 0.080 g of the desired product as a brown powder (19%). $^1$H NMR (299.817 MHz, 20° C., CD$_2$Cl$_2$): 20.583 and 20.577 [two s, two orientations of Ru=CH$_\alpha$], 8.54 [br s], 7.60 [t, J=7.3], 7.34 (t, J=7.8], 5.16 (qt, J=5.1], 3.46-3.96 [m], 2.86 (t, J=12.4], 2.34-2.50 [m], 1.44-2.20 [m], 1.43 (s), 1.41 (s), 0.82-1.31 [m], 1.26 [s], 1.12 [s], 1.01 [s], 0.57 [d, J=6.9], 0.25 [s]. $^1$H NMR (299.817 MHz, −70° C., CD$_2$Cl$_2$): 20.32 [s, Ru=CH$_\alpha$], 9.07 [d, J=7.8], 7.87 [t, J=7.1], 7.59 [t, J=7.4], 7.35 [m], 4.92 [br], 3.30-3.90 [m], 2.69 [m], 2.44-0.78 [m], 1.33 [s], 1.16 [s], 1.02 [s], 0.90 [s], 0.88 [s], 0.86 [s], 0.80 [s], 0.78 [s], 0.43 [s], 0.11 [br d, J=5.7]. $^{31}$P {$^1$H} MR (121.39 MHz, 25° C., CD$_2$Cl$_2$): 21.72 [s]. $^{31}$P {$^1$H} NMR (121.39 MHz, −65° C., CD$_2$Cl$_2$): 21.95 [s], 21.16 [s].

(b-ii) 2-tert-butoxy-1,3-bis[2',6'-dimethyl-3'-(2",6"-dimethylphenyl)phenyl]-4,5-dihydroimidazol-2-ylidene was prepared by stirring a suspension of potassium tert-butoxide (9 mg, 0.080 mmol) and 1,3-bis[2',6'-dimethyl-3'-(2",6"-dimethylphenyl)-phenyl]-4,5-dihydroimidazol-2-ylidene (50 mg, 0.079 mmol) in benzene (1 mL) for 1 h at room temperature. To this suspension was added phenylmethylene-bis(tricyclohexylphosphine) ruthenium dichloride (65 mg, 0.079 mmol) in benzene (1 mL). The solution, which immediately became pinkish purple, was stirred at 50° C. for 16 h. After this time, the solution was cooled and the solvent was evaporated to near dryness. The residue was passed through a plug of TSI silica gel, using 1:1 ether/pentane as the eluant. After concentrating, the solids were washed with pentane (5×1 mL). The solid material was dissolved in benzene (1 mL) and was frozen (dry ice/acetone). The solvent was removed by sublimation to give phenylmethylene 1,3-bis[2',6'-dimethyl-3'-(2",6"-dimethyl-phenyl)phenyl]-4,5-dihydroimidazol-2-ylidene (50 mg, 62%) as a pink solid. $^1$H NMR (500 mHz, toluene-d$_8$): δ=19.46 (s, 1H), 9.59 (br s, 1H), 7.35-6.18 (multiple peaks, 14H), 3.68-3.22 (multiple peaks, 4H), 2.98 (s, 3H), 2.61 (s, 3H), 2.46 (s, 3H), 2.35 (s, 3H), 2.19 (s, 3H), 1.98 (s, 3H), 1.92 (s, 3H), 2.09-1.10 (multiple peaks, 36H) ppm. $^{31}$P NMR (202 mHz, toluene-d$_8$): δ=34.54 ppm (s).

The same procedures may be followed for preparation of a ruthenium catalyst containing other ligands.
Representative cross-metathesis reactions using the catalysts prepared in (b-i) and (b-ii):

(c-i) Upon isolation of the catalyst prepared with the 1,3-(+)diisopinocamphenyl-4,5-dihydroimidazole-2-ylidene ligand as described in (b), a representative cross-metathesis reaction can be conducted with 5 mol % of the catalyst in a reaction with a 2:1 ratio of cis-2-butene-1,4-diacetate and an α-terminal olefin at 40° C. in methylene chloride for 12 hours to generate the cross-metathesis allylic acetate product as a 1.3:1 mixture of trans and cis isomers in 85% overall yield. Upon isolation of the second catalyst prepared as described in (a), i.e., phenylmethylene 1,3-bis[2',6'-dimethyl-3'-(2",6"-dimethylphenyl)phenyl]-4,5-dihydroimidazol-2-ylidene tricyclohexylphosphine ruthenium dichloride, a representative cross-metathesis reaction can be conducted with 5 mol % of the catalyst in a reaction with a 2:1 ratio of cis-2-butene-1,4-diacetate and an α-terminal olefin at 40° C. in methylene chloride for 6 hours to generate the cross-metathesis allylic acetate product as a 2.2:1 mixture of trans and cis isomers in 60% overall yield.

(c-ii) Allylbenzene (15 mg, 0.13 mmol), cis-1,4-diacetoxy-2-butene (45 mg, 0.26 mmol), and phenylmethylene 1,3-bis [2',6'-dimethyl-3'-(2",6"-dimethylphenyl)phenyl]-4,5-dihydroimidazol-2-ylidene (4 mg, 0.004 mmol) were dissolved in CD$_2$Cl$_2$ (0.7 mL) and added to a screw-cap NMR tube. The tube was heated at 40° C. and the reaction progress was monitored periodically by NMR. After 12 h at 40° C., NMR analysis indicated that the reaction had proceeded to 77% completion. The tube was cooled to room temperature and the solution was transferred to a 5 mL flask and the solvent was removed in vacuo. The residue was taken up in CH$_2$Cl$_2$ and passed through a small plug of silica. The solution was concentrated and the residue was taken up in CDCl$_3$ and was added to an NMR tube. NMR analysis indicated a 2.4:1 (E:Z) ratio of E/Z-1-acetoxy-4-phenyl-2-butene.

EXAMPLE 9

Allylboronates as Cross-Metathesis Substrates

General procedures for carrying out cross-metathesis reactions with pinacol allyl boronate: A flame-dried round-bottomed flask was charged with pinacol allyl boronate (1 eq.) and the olefin cross partner CH$_2$=CHR (3.0 equiv.). A rubber septum was attached, dichloromethane was added (0.2-0.3 N in pinacol allyl boronate), and argon was bubbled through the resultant solution for 10 min. Under a stream of argon, catalyst (5) (0.050 equiv.) was added to the degassed solution as a solid. A reflux condenser was attached immediately, and the entire system was flushed with argon for 2 min. The colored solution was then heated at reflux for 2-12 h, and the reaction was monitored by thin-layer chromatography. Upon consumption of the allylboronate reactant, the aldehyde R'CHO (1.5 eq.) was added to the reaction mixture through a syringe, and the resultant solution was stirred at 23° C. in vacuo, and the residue was purified by means of silica gel chromatography to yield the allylic alcohol product having the structure CH$_2$=CHR—CH(OH)—R'.

We claim:

1. A method for synthesizing a functionalized olefin via a cross-metathesis reaction, comprising contacting (a) a first olefinic reactant with (b) a second olefinic reactant in the presence of (c) a catalyst composed of a Group 8 transition metal alkylidene complex under conditions and for a time period effective to allow cross-metathesis to occur, wherein the catalyst has the structure of formula (VIC)

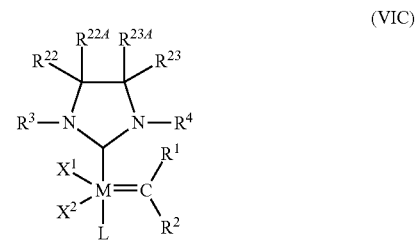

in which:
M is Ru;
X$^1$ and X$^2$ are independently selected from the group consisting of halide, CF$_3$CO$_2$, CH$_3$CO$_2$, CFH$_2$CO$_2$, (CH$_3$)$_3$CO, (CF$_3$)$_2$(CH$_3$)CO, (CF$_3$)(CH$_3$)$_2$CO, PhO, MeO, EtO, tosylate, mesylate, and trifluoromethanesulfonate;
R$^1$ is hydrogen and R$^2$ is selected from the group consisting of C$_1$-C$_{20}$ alkyl, C$_2$-C$_{20}$ alkenyl, and aryl;
L is a neutral electron donor ligand selected from the group consisting of phosphine, phosphite, phosphinite, phosphonite, ether, amine, amide, imine, carboxyl, pyridine, substituted pyridine, imidazole, and substituted imidazole;

R$^3$ and R$^4$ are aromatic, substituted aromatic, heteroaromatic, substituted heteroaromatic, alicyclic, substituted alicyclic, heteroatom-containing alicyclic, or substituted heteroatom-containing alicyclic, composed of from one to about five rings; and R$^{22}$ and R$^{23}$, are hydrogen, and R$^{22A}$ and R$^{23A}$ are selected from hydrogen, lower alkyl and phenyl, or are linked to form a cyclic group; and wherein any two or more of X$^1$, X$^2$, L, R$^1$, R$^2$, R$^3$, and R$^4$ can be taken together to form a chelating multidentate ligand;

wherein the first olefinic reactant has the structure of formula (VIII)

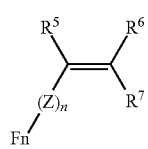

(VIII)

wherein:
R$^5$, R$^6$ and R$^7$ are independently selected from the group consisting of hydrogen, hydrocarbyl, substituted hydrocarbyl, heteroatom-containing hydrocarbyl, substituted heteroatom-containing hydrocarbyl, and —(Z)$_n$,-Fn, where n is zero or 1;

Z is selected from the group consisting of hydrocarbylene and substituted hydrocarbylene linking group; and Fn is a functional group selected from phosphonato;

wherein the second olefinic reactant has the molecular structure R$^{18}$R$^{19}$C═CR$^{20}$R$^{21}$, wherein R$^{18}$, R$^{19}$, R$^{20}$, and R$^{21}$ are independently selected from the group consisting of hydrogen, hydrocarbyl, substituted hydrocarbyl, heteroatom-containing hydrocarbyl, and substituted heteroatom-containing hydrocarbyl.

2. The method of claim 1, wherein:
R$^1$ is hydrogen, and R$^2$ is phenyl, vinyl, methyl, isopropyl, or t-butyl, optionally substituted with one or more moieties selected from the group consisting of C$_1$-C$_6$ alkyl, C$_1$-C$_6$ alkoxy, phenyl, and a functional group Fn; and
L is a phosphine of the formula PR$^{27}$R$^{28}$R$^{29}$, where R$^{27}$, R$^{28}$, and R$^{29}$ are each independently aryl or C$_1$-C$_{10}$ alkyl.

3. The method of claim 2, wherein:
L is selected from the group consisting of —P(cyclohexyl)$_3$, —P(cyclopentyl)$_3$, —P(isopropyl)$_3$, —P(phenyl)$_3$, —P(phenyl)$_2$(R$^7$) and —P(phenyl)(R$^7$)$_2$, in which R$^7$ is lower alkyl; and
R$^3$ and R$^4$ are the same and are either aromatic or C$_7$-C$_{12}$ alicyclic, if aromatic, each having the structure of formula (XI)

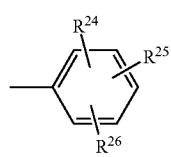

(XI)

in which R$^{24}$, R$^{25}$, and R$^{26}$ are each independently hydrogen, C$_1$-C$_{10}$ alkyl, C$_1$-C$_{10}$ alkoxy, aryl, substituted aryl, halogen, or a functional group.

4. The method of claim 3, wherein:
X$^1$ and X$^2$ are halide;
R$^2$ is phenyl or —CH═C(CH$_3$)$_2$;
R$^3$ and R$^4$ are mesityl, diisopinocamphenyl, or 2,4,2',6'-tetramethylbiphenylyl;
L is selected from the group consisting of —P(cyclohexyl)$_3$ and —P(cyclopentyl)$_3$; and
R$^{22}$ and R$^{23}$ are hydrogen.

5. The method of claim 1, wherein R$^5$, R$^6$ and R$^7$ are hydrogen, n is zero, and Fn is phosphonato, such that the first olefinic reactant is a vinylphosphonate having the structure of formula (XII)

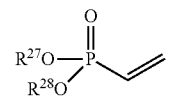

(XII)

wherein R$^{27}$ and R$^{28}$ are hydrocarbyl.

6. The method of claim 1, wherein for the first olefinic reactant, R$^5$, R$^6$ and R$^7$ are hydrogen, n is 1, and Fn is selected from the group consisting of phosphonato.

7. The method of claim 6, wherein Fn is phosphonato, such that the first olefinic reactant is an allylphosphonate having the structure of formula (XIII)

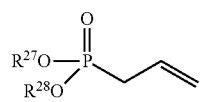

(XIII)

wherein R$^{27}$ and R$^{28}$ are hydrocarbyl.

8. The method of claim 1, wherein the catalyst is selected from

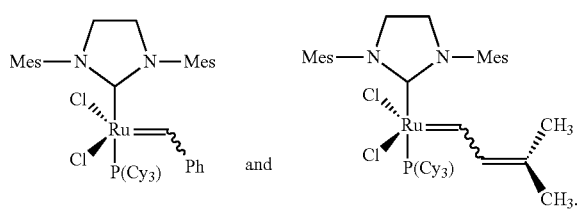

* * * * *